US010378034B2

(12) United States Patent
Ræder et al.

(10) Patent No.: US 10,378,034 B2
(45) Date of Patent: Aug. 13, 2019

(54) **USE OF A N-ACETYLNEURAMINATE LYASE DERIVED FROM THE BACTERIUM *ALIIVIBRIO SALMONICIDA* IN THE PRODUCTION OF NEURAMINIC ACID AND DERIVATIVES THEREOF**

(71) Applicant: Universitetet i Tromsø-Norges Arktiske Universitet, Tromsø (NO)

(72) Inventors: Inger Lin Uttakleiv Ræder, Tromsø (NO); Bjørn Altermark, Tromsø (NO); Man Kumari Gurung, Tromsø (NO); Arne Oskar Smalås, Kvaløysletta (NO)

(73) Assignee: Universitetet i Tromsø—Norges Arktiske Universitet, Tromsø (NO)

( * ) Notice: Subject to any disclaimer, the term of this patent is extended or adjusted under 35 U.S.C. 154(b) by 58 days.

(21) Appl. No.: 15/313,915

(22) PCT Filed: May 27, 2015

(86) PCT No.: PCT/NO2015/050091
§ 371 (c)(1),
(2) Date: Nov. 23, 2016

(87) PCT Pub. No.: WO2015/183099
PCT Pub. Date: Dec. 3, 2015

(65) Prior Publication Data
US 2017/0175155 A1 Jun. 22, 2017

(30) Foreign Application Priority Data
May 27, 2014 (NO) .................................. 20140655

(51) Int. Cl.
*C12N 9/88* (2006.01)
*C12P 19/26* (2006.01)
*C12Q 1/527* (2006.01)

(52) U.S. Cl.
CPC ............... *C12P 19/26* (2013.01); *C12N 9/88* (2013.01); *C12Q 1/527* (2013.01); *C12Y 401/03003* (2013.01); *C12Y 403/03001* (2013.01)

(58) Field of Classification Search
CPC combination set(s) only.
See application file for complete search history.

(56) References Cited

U.S. PATENT DOCUMENTS

| 5,665,574 A | 9/1997 | Tsukada et al. |
| 6,156,544 A | 12/2000 | Dawson et al. |
| 2013/0266987 A1 | 10/2013 | Mach-Aigner et al. |

FOREIGN PATENT DOCUMENTS

| CN | 1584015 A | 2/2005 | |
| CN | 101165190 B | 8/2011 | |
| CN | 102649965 A | 8/2012 | |
| EP | 0164754 A1 | 12/1985 | |
| JP | 61-219384 A | 9/1986 | |
| JP | 62-122584 A | 6/1987 | |
| WO | 2002/33070 A1 | 4/2002 | |
| WO | 2003/072783 A1 | 9/2003 | |
| WO | 2008/040717 A2 | 4/2008 | |
| WO | 2008/097366 A2 | 8/2008 | |
| WO | 2010/052324 A1 | 5/2010 | |
| WO | 2011/086834 A1 | 7/2011 | |
| WO | WO-2011086834 A1 * | 7/2011 | ............... C12N 9/88 |
| WO | 2011/130836 A1 | 10/2011 | |
| WO | 2013/088267 A1 | 6/2013 | |

OTHER PUBLICATIONS

Isafumi Maru et al Simple and large-scale production of N-acetylneuraminic acid from N-acetyl-dglucosamineand pyruvate using N-acyl-dglucosamine 2-epimerase and N-acetylneuraminate lyase. Carbohydrate Research 306 1998 575-578. (Year: 1998).*
Blayer et al. Alkaline catalysis or the direct synthesis of N-acetyl-D-neuraminic acid (Neu5AC) from N-acetyl-D-glucosamine (GlucNAc), Biotechnol. Bioeng. 1999, vol. 66, No. 2, p. 131-136. (Year: 1999).*
Hjerde et al. ("The genome sequence of the fish pathogen *Aliivibrio salmonicida* strain LFI1238 shows extensive evidence of gene decay." Genomics 9:616-616(2008). (Year: 2008).*
Aminoff, D., "Methods for the Quantitative Estimation of N-acetylneuraminic Acid and their Application to Hydrolysates of Sialomucoids", Biochem. J., vol. 81, 1961, pp. 384-392.
Auge et al., "Synthesis with Immobilized Enzyme of the Most Important Sialic Acid", Tetrahedron Letters, vol. 25, 1984, pp. 4663-4664.
Blayer et al., "Alkaline Biocatalysis for the Direct Synthesis of N-Acetyl-D-Neuraminic Acid (Neu5ac) from N-Acetyl-D-Glucosamine (Glcnac)." Biotechnology and Bioengineering, vol. 66, No. 2, 1999, pp. 131-136.
Brug et al., "Configuration of N-Acetylneuraminic Acid", Nature, vol. 182, No. 4643, Oct. 25, 1958, pp. 1159-1160.
Chou et al., "Modulation of Substrate Specificities of D-Sialic Acid Aldolase through Single Mutations of Val-251", The Journal of Biological Chemistry, vol. 286, No. 16, Apr. 22, 2011, pp. 14057-14064.
Comb et al., "Composition and Enzymatic Synthesis of N-Acetylneuraminic Acid (Sialic Acid)", Journal of the American Chemical Society, vol. 80, No. 1, Jan. 20, 1958, pp. 497-499.

(Continued)

*Primary Examiner* — Kagnew H Gebreyesus
(74) *Attorney, Agent, or Firm* — Morrison and Foerster LLP

(57) ABSTRACT

The present invention provides to methods for the production of neuraminic acid or derivatives thereof under alkaline conditions and to the use of neuraminate lyases showing improved characteristics under alkaline conditions in the production of neuraminic acid or its derivatives. More particularly, the present invention employs inter alia a N-acetylneuraminate lyase which has been isolated from the psychrophilic bacterium *Aliivibrio salmonicida* LFI1238 and has shown to have improved characteristics under alkaline conditions.

12 Claims, 18 Drawing Sheets

Specification includes a Sequence Listing.

(56) References Cited

OTHER PUBLICATIONS

Comb et al., "The Sialic Acids. I. The structure and Enzymatic Synthesis of N-Acetylneuraminic Acid", The Journal of Biological Chemistry, vol. 235, No. 9, Sep. 1960, pp. 2529-2537.
Ericsson et al., "Thermofluor-Based High-Throughput Stability Optimization of Proteins for Structural Studies", Analytical Biochemistry vol. 357, No. 2, Oct. 15, 2006, pp. 289-298.
Genbank, "N-Acetylneuraminate Lyase Fra Aliivibrio Logei", Accession No. WP_017023042.1, Available online at <https://www.ncbi.nlm.nih.gov/protein/WP_017023042.1, Jun. 27, 2013, 1 page.
Genbank, "N-Acetylneuraminate Lyase Fra Aliivibrio Salmonicida", Accession No. WP_012549679.1, Available online at <https://www.ncbi.nlm.nih.gov/protein/WP_012549679,1>, May 25, 2013, 1 page.
Genbank, "N-Acetylneuraminate Lyase Fra Vibrio Fischeri", Accession No. ACH65343.1, Available online at https://www.ncbi.nlm.nih.gov/protein/ACH65343.1, Jan. 31, 2014, 1 page.
Gurung et al., "Characterization of the Sialic Acid Synthase from Aliivibrio Salmonicida suggests a Novel Pathway for Bacterial Synthesis of 7-0-Acetylated Sialic Acids", Giycobiology, vol. 23, No. 7, Mar. 11, 2013, pp. 806-819.
Gurung et al., "Features and Structure of a Sialic Acid Aldolase from Aliivibrio Salmonicida. Poster Session. P12", Bioprosp 15. the 7th International Conference on Marine Bioprospecting, Feb. 20, 2015, (Abstract Only).
Hjerde et al., "The Genome Sequence of the Fish Pathogen *Aliivibrio salmonicida* Strain LFI1238 Shows Extensive Evidence of Gene Decay", BMC Genomics, vol. 9, No. 616, 2008, pp. 1-14.
International Preliminary Report on Patentability received for PCT Application No. PCT/NO2015/050091, dated Dec. 8, 2016, 10 pages.
International Search Report and Written Opinion received for PCT Patent Application No. PCT/NO2015/050091, dated Oct. 6, 2015, 14 pages.
Koeller et al,, "Enzymes for Chemical Synthesis", Nature vol. 409, No. 6817, Jan. 11, 2001, pp. 232-240.
Komaki et al., "Purification and Characterization of N-Acetylneuraminate Synthase from *Escherichia coli* KI-M12", Bioscience, Biotechnology and Biochemistry, vol. 61, No. 12, 1997, pp. 2046-2050.
Li et al., "Pasteurella Multocida Sialic Acid Aldolase: A Promising Biocatalyst." Applied Microbiology and Biotechnology, vol. 79, No. 6, Jul. 2008, pp. 963-970.
Machajewski et al.,"The Catalytic Asymmetric Aldol Reaction", Angewandte Chemie (International Edition in English), vol. 39, No. 8, Apr. 17, 2000, pp. 1352-1375.
Sanchez-Carron et al., "Molecular Characterization of a Novel N-Acetylneuraminate Lyase from *Lactobacillus plantarum* Wcfs1", Applied and Environmental Microbiology, vol. 77, No. 7, Apr. 2011, pp. 2471-2478.
Search Report received for Norwegian Patent Application No. 20140655, dated Oct. 28, 2014, 2 pages.
Uniprot, "Database accession No. B6EI04", Available online at <http://www.uniprot.org/uniprot/B6EI04.txt, Nov. 25, 2008, 2 pages.
Wang et al., "Production of 2-Keto-3-Deoxy-D-Glycero-D-Galacto-Nonopyranulosonic Acid (Kdn) Using Fusion Protein of N-Acetyl-D-Neuraminic Acid Aldolase", Biochemical Engineering Journal, vol. 29, 2006, pp. 75-80.
Warren et al., "The Biosynthesis of Sialic Acids", The Journal of Biological Chemistry, vol. 237, No. 5, May 1962, pp. 1421-1431.
Warren, Leonard, "The Thiobarbituric Acid Assay of Sialic Acids", The Journal of Biological Chemistry, vol. 234, No. 8, Aug. 1959, pp. 1971-1975.

\* cited by examiner

SEQUENCE LISTING

<160> NUMBER OF SEQ ID NOS: 9

<210> SEQ ID NO 1
<211> LENGTH: 297
<212> TYPE: PRT
<213> ORGANISM: Aliivibrio salmonicida

<400> SEQUENCE: 1

```
Met Lys Lys Leu Thr Gly Leu Ile Ala Ala Pro His Thr Pro Phe Asp
1               5                   10                  15

Ser Ser Ser Asn Val Asn Phe Glu Glu Ile Asp Lys Ile Ala Lys His
            20                  25                  30

Leu Ile Asn Asp Gly Val Lys Gly Ile Tyr Val Cys Gly Thr Thr Gly
        35                  40                  45

Glu Gly Ile His Cys Ser Val Glu Arg Lys Ala Ile Ala Glu Arg
    50                  55                  60

Trp Val Ser Ala Cys Asn His Lys Leu Asp Ile Ile Val His Thr Gly
65                  70                  75                  80

Ala Leu Ser Ile Val Asp Thr Leu Glu Leu Thr Arg His Ala Asp Thr
                85                  90                  95

Leu Asp Ile Leu Ala Thr Ser Ala Ile Gly Pro Cys Phe Phe Lys Pro
```

```
            100                 105                 110
Gly Ser Val Ser Asp Leu Val Glu Tyr Cys Ala Thr Ile Ala Ala Ala
        115                 120                 125

Ala Pro Ser Lys Gly Phe Tyr Tyr Tyr His Ser Gly Met Ser Gly Val
130                 135                 140

Asn Leu Asn Met Glu Glu Phe Leu Ile Gln Ala Asp Lys Arg Ile Pro
145                 150                 155                 160

Asn Leu Ser Gly Leu Lys Phe Asn Ser Gly Asp Leu Tyr Glu Tyr Gln
                165                 170                 175

Arg Cys Leu Arg Ala Cys Asp Gly Lys Phe Asp Val Pro Phe Gly Val
                180                 185                 190

Asp Glu Phe Leu Pro Gly Ala Leu Ala Val Gly Ala Lys Ser Ala Val
                195                 200                 205

Gly Ser Thr Tyr Asn Tyr Ala Ala Pro His Phe Asn Ser Ile Ile Glu
        210                 215                 220

Ala Phe Asn Lys Gly Asp His Asp Ala Val Phe Asn Lys Met Thr Asn
225                 230                 235                 240

Val Ile Glu Leu Ile Arg Val Leu Val Glu Phe Gly Gly Val Ala Ala
                245                 250                 255

Gly Lys Ile Ala Met Glu Leu His Asp Ile Asn Ala Gly Asp Pro Arg
                260                 265                 270

Leu Pro Leu Met Pro Leu Ser Ala Glu Gln Lys Leu Thr Val Val Glu
                275                 280                 285

Lys Met Arg Ala Ala Asn Phe Leu Lys
                290                 295

<210> SEQ ID NO 2
<211> LENGTH: 49
<212> TYPE: DNA
<213> ORGANISM: Artificial Sequence
<220> FEATURE:
<223> OTHER INFORMATION: PCR primer

<400> SEQUENCE: 2
ttcgaaaacc tgtatttca gggcatgaaa aagttaacag gtttaattg              49

<210> SEQ ID NO 3
<211> LENGTH: 40
<212> TYPE: DNA
<213> ORGANISM: Artificial Sequence
<220> FEATURE:
<223> OTHER INFORMATION: PCR primer

<400> SEQUENCE: 3
ggggacaagt ttgtacaaaa aagcaggctt cgaaaacctg                       40

<210> SEQ ID NO 4
<211> LENGTH: 37
<212> TYPE: DNA
<213> ORGANISM: Artificial Sequence
<220> FEATURE:
<223> OTHER INFORMATION: PCR primer

<400> SEQUENCE: 4
ggagatagaa ccatgaaaaa gttaacaggt ttaattg                          37

<210> SEQ ID NO 5
<211> LENGTH: 46
<212> TYPE: DNA
<213> ORGANISM: Artificial Sequence
```

```
<220> FEATURE:
<223> OTHER INFORMATION: PCR primer

<400> SEQUENCE: 5
ggggacaagt tgtacaaaa aagcaggctt cgaaggagat agaacc                    46

<210> SEQ ID NO 6
<211> LENGTH: 37
<212> TYPE: DNA
<213> ORGANISM: Artificial Sequence
<220> FEATURE:
<223> OTHER INFORMATION: PCR primer

<400> SEQUENCE: 6
gaaagctggg tgttatttaa gaaaatttgc ggctctc                             37

<210> SEQ ID NO 7
<211> LENGTH: 33
<212> TYPE: DNA
<213> ORGANISM: Artificial Sequence
<220> FEATURE:
<223> OTHER INFORMATION: PCR primer

<400> SEQUENCE: 7
ggggaccact tgtacaaga aagctgggtg tta                                  33

<210> SEQ ID NO 8
<211> LENGTH: 43
<212> TYPE: DNA
<213> ORGANISM: Artificial Sequence
<220> FEATURE:
<223> OTHER INFORMATION: PCR primer

<400> SEQUENCE: 8
ttagtggtgg tggtggtggt gtttaagaaa atttgcggct ctc                      43

<210> SEQ ID NO 9
<211> LENGTH: 50
<212> TYPE: DNA
<213> ORGANISM: Artificial Sequence
<220> FEATURE:
<223> OTHER INFORMATION: PCR primer

<400> SEQUENCE: 9
gggaccactt tgtacaagaa agctgggtct tagtggtggt ggtggtggtg               50
```

USE OF A N-ACETYLNEURAMINATE LYASE DERIVED FROM THE BACTERIUM *ALIIVIBRIO SALMONICIDA* IN THE PRODUCTION OF NEURAMINIC ACID AND DERIVATIVES THEREOF

CROSS REFERENCE TO RELATED APPLICATIONS

This application is a U.S. National Phase patent application of PCT/N02015/050091, filed on May 27, 2015, which claims priority to Norwegian Patent Application No. 20140655, filed on May 27, 2014, the disclosures of which are hereby incorporated by reference in the present disclosure in their entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 699132003700SEQLIST.txt, date recorded: Nov. 21, 2016, size: 5 KB).

FIELD OF THE INVENTION

The present invention provides to methods for the production of neuraminic acid or derivative thereof under alkaline conditions and to the use of neuraminate lyases showing improved characteristics under alkaline conditions in the production of neuraminic acid or its derivatives. More particularly, the present invention employs inter alia a N-acetylneuraminate lyase which has been isolated from the psychrophilic bacterium *Aliivibrio salmonicida* LFI1238 and has shown to have improved characteristics under alkaline conditions.

BACKGROUND OF THE INVENTION

In the last few decades, substantial and continuous works within the field of sialobiology have shed light on the importance of sialic acids in the biology of both eukaryotes and prokaryotes. In eukaryotes, sialic acids are involved in the regulation of important biological functions, but they are also involved in interactions with bacteria and viruses. A few pathogenic bacteria decorate themselves with sialic acids on their surfaces to avoid the host immune system, whereas many viruses use these sugars as receptors to enter the host.

Sialic acids are sugars found on the surface of both prokaryotic- and eukaryotic cells and belong to the family of nine carbon α-keto acidic monosaccharides. N-acetylneuraminic acid (Neu5Ac) is the most frequent sugar among this family. Extensive research has been done after the discovery of the Neu5Ac in 1936 due to its interesting and important biological roles. The application of sialic acid and its derivatives are growing; they are used in diagnostic research because an elevated concentration of free serum sialic acid is indicative of several diseases, the concept of sialic acid as a glyconutrient is emerging due to the fact that it is important in fetal brain development and analogues of sialic acids are considered potential antiviral agents. One of the most successful examples of the latter is Zanamivir. Consisting of a simple modification of Neu5Ac it inhibits neuraminidases of both influenza virus A and B, and it is also used commercially as protection against the highly virulent H5N1 strain (birdflu).

Many promising therapeutic applications of Neu5Ac have led to an increased interest in developing efficient methods for its production. Isolation of Neu5Ac from natural sources such as egg yolk, edible bird's nest and milk is hampered by low yields, hence, inappropriate for large scale production. Neu5Ac can be produced by de novo chemical synthesis. However, the structural features of the molecule render inherent challenges concerning the correct stereospecificity. Chemoenzymatic synthesis has been reported, but the subsequent steps of chemical addition can be cumbersome. Therefore, highly stereospecific and simple enzymatic methods are economically, and perhaps also environmentally better alternatives for large scale production of Neu5Ac, since the enzyme catalyzed reaction result in the formation of stereo- and regiochemically defined products with significant rate acceleration (Koeller and Wong, 2001).

Sialic acid synthase and N-acetylneuraminate lyase (NAL, or sialic acid aldolase), are enzymes which can produce N-acetylneuraminic acid by the condensation of N-acetylmannosamine (ManNAc) with phosphoenolpyruvate (PEP) (Warren and Felsenfeld, 1962) or pyruvate, respectively.

Sialic acid synthase has been recombinantly produced from different organisms, among others *Aliivibrio salmonicida* (Gurung et al., 2013). However, there is no report of commercial availability of this enzyme for use in industrial scale. This is probably due to the high cost of the cofactor PEP. NAL, on the other hand, is an enzyme which is available commercially and is being used to produce Neu5Ac and its analogues. It is a class I lyase/aldolase which catalyzes the reversible cleavage of Neu5Ac to yield pyruvate and ManNAc, with an equilibrium favoring Neu5Ac cleavage* (Brug and Paerels, 1958; Comb and Roseman, 1958). Its biological role is to cleave Neu5Ac, however, at favorable conditions, the reverse aldol condensation reaction can be utilized in vitro to synthesize Neu5Ac and its derivatives from pyruvate and ManNAc (Auge et al., 1984). The use of NAL instead of sialic acid synthase to produce Neu5Ac commercially is favorable because of the relatively low price of pyruvate compared to PEP. In addition, NALs generally tolerate a wide range of acceptor substrates which can be useful for synthesis of Neu5Ac analogues (Machajewski and Wong, 2000).

The production of Neu5Ac through the NAL synthetic reaction is sometimes coupled with an alkaline or enzymatic epimerization of N-acetylglucosamine (GlcNAc) to N-acetylmannosamine as a first step, because GlcNAc is a significantly cheaper starting material than ManNAc and the production costs will be reduced. This chemical epimerization is performed under alkaline conditions (above pH 9). Known NALs from e.g. *E. coli*, Clostridium perfringens or *Pasteurella multocida* however are typically active at a pH ranging from 7 to 9. Under alkaline conditions, however, these NALs are not only are unstable, but also loose activity to a great extent (Blayer et al., 1999). Hence, the unfavourable stability and activity profiles seen for these enzymes under alkaline conditions provides a boundary to the operating conditions involved in an integrated alkaline epimerization and NAL-catalyzed biotransformation process.

Thus, there is a need in the art for methods which can provide neuraminic acid or derivatives thereof such as N-acetylneuraminic acid (Neu5Ac) in high yield and in a more cost-effective manner.

SUMMARY OF THE INVENTION

The present invention addresses the foregoing needs by providing inter alia methods employing a N-acetylneuraminate lyase which has been isolated from the psychrophilic bacterium *Aliivibrio salmonicida* LFI1238 and has shown to have improved characteristics under alkaline conditions.

According to one aspect, the present invention provides a method for the production of neuraminic acid or a derivative thereof comprising:

a) optionally, transforming glucosamine or a derivative thereof into mannosamine or derivative thereof by epimerization at an alkaline pH of at least about 9; and b) reacting mannosamine or a derivative thereof with pyruvate at an alkaline pH of at least about 9 in the presence of a polypeptide comprising the amino acid sequence as set forth in SEQ ID NO: 1 or a functional variant thereof; wherein the functional variant is a polypeptide comprising an amino acid sequence having at least about 90% sequence identity to the amino acid sequence set forth in SEQ ID NO: 1.

According to certain embodiments, the functional variant is a polypeptide comprising an amino acid sequence having at least about 95%, at least about 96%, at least about 97%, at least about 98%, or at least about 99%, sequence identity to the amino acid sequence set forth in SEQ ID NO: 1.

According to particular embodiments, the functional variant has at least one of the following properties i) to iii):

i) a pH optimum for the condensation reaction of about 7.5 to about 8;

ii) the activity ($\mu$mol min$^{-1}$) of the condensation reaction is retained at a level of at least 80%, such as at least about 83%, at least about 85% or at least about 90%, of the initial activity following storage for 30 days at 23° C. in glycine buffer at pH 11;

iii) a specific activity of the condensation reaction in the range from about 0.0435 to about 0.0725 $\mu$mol min$^{-1}$ mg$^{-1}$, such as in the range from about 0.0522 to about 0.0638 $\mu$mol min$^{-1}$ mg$^{-1}$, such as about 0.058 $\mu$mol min$^{-1}$ mg$^{-1}$.

The specific activity of the condensation reaction may be (e.g., is) measured after 30 minutes incubation at 23° C. employing 7 $\mu$g polypeptide, 20 mM N-acetylmannosamine, 80 mM pyruvate and 124 mM HEPES, pH 8.0, in a total of 250 $\mu$l reaction mixture.

According to certain embodiments, the derivative of neuraminic acid produced is an N- or O-substituted neuraminic acid, such as an N-acetylated or N-glycolylated neuraminic acid.

According to particular embodiments, the derivative of neuraminic acid is N-acetylneuraminic acid (Neu5Ac) or an O-substituted derivative thereof, such as an O-acetyl derivative thereof, such as 7-O-acetyl-N-acetylneuraminic acid (Neu5, 7Ac2) or 9-O-acetyl-N-acetylneuraminic acid (Neu5, 9 Ac2).

According to more particular embodiments, the derivative of neuraminic acid is N-acetylneuraminic acid (Neu5Ac).

According to other particular embodiments, the derivative of neuraminic acid is N-glycolylneuraminic acid (Neu5Gc) or an O-substituted derivative thereof, such as an O-acetyl derivative thereof, such as 7-O-acetyl-N-glycolylneuraminic acid (Neu5, 7Gc2) or 9-O-acetyl-N-acetylneuraminic acid (Neu5, 9 Gc2).

According to other more particular embodiments, the derivative of neuraminic acid is N-glycolylneuraminic acid (Neu5Gc).

According to particular embodiments, the derivative of neuraminic acid is Neu5Ac; legionaminic acid; Neu5,7Ac2, Neu5,8Ac2, Neu5,9Ac2 or any mixture thereof; Neu5Gc; 2-keto-3-deoxy-D-glycero-D-galacto-nononic acid; or any mixture thereof.

According to more particular embodiments, the derivative of neuraminic acid is Neu5Ac; legionaminic acid; Neu5, 7Ac2, Neu5,8Ac2, Neu5,9Ac2 or any mixture thereof; or any mixture thereof.

According to certain embodiments, the derivative of mannosamine is an N- or O-substituted mannosamine, such as an N-acetylated or N-glycolylated mannosamine.

According to particular embodiments, the derivative of mannosamine is N-acetylmannosamine (ManNAc) or an O-substituted derivative thereof, such as an O-acetylated derivative thereof, such as 4-O-acetyl-N-acetylmannosamine, 6-O-acetyl-N-acetylmannosamine or 9-O-acetyl-N-acetylmannosamine.

According to more particular embodiments, the derivative of mannosamine is N-acetylmannosamine (ManNAc).

According to other particular embodiments, the derivative of mannosamine is N-glycolylmannosamine (ManNGc) or an O-substituted derivative thereof, such as an O-acetyl derivative thereof, such as 4-O-acetyl-N-glycolylmannosamine, 6-O-acetyl-N-glycolylmannosamine or 9-O-acetyl-N-glycolylmannosamine.

According to other more particular embodiments, the derivative of mannosamine is N-glycolylmannosamine (ManNGc).

According to particular embodiments, the derivative of mannosamine is ManNAc; 2,4-diacetamino-2,4,6-trideoxymannose; 4-O-acetyl-2-N-acetylmannosamine, 6-O-acetyl-2-N-acetylmannosamine or any mixture thereof; N-glycolylmannosamine; D-mannose; or any mixture thereof.

According to more particular embodiments, the derivative of mannosamine is ManNAc; 2,4-diacetamino-2,4,6-trideoxymannose; 4-O-acetyl-2-N-acetylmannosamine, 6-O-acetyl-2-N-acetylmannosamine or any mixture thereof; or any mixture thereof.

According to certain embodiments, the derivative of glucosamine is an N-substituted glucosamine, such as an N-acetylated or N-glycolylated glucosamine.

According to particular embodiments, the derivative of glucosamine is N-acetylglucosamine (GlcNAc) or an O-substituted derivative thereof, such as an O-acetyl derivative thereof, such as an 4-O-acetyl-N-acetyl glucosamine, 6-O-acetyl-N-acetylglucosamine or 9-O-acetyl-N-acetylglucosamine.

According to more particular embodiments, the derivative of glucosamine is N-acetylglucosamine (GlcNAc).

According to other particular embodiments, the derivative of glucosamine is N-glycolylglucosamine (GlcNGc) or an O-substituted derivative thereof, such as an O-acetyl derivative thereof, such as 4-O-acetyl-N-glycolylmannosamine, 6-O-acetyl-N-glycolylmannosamine or 9-O-acetyl-N-glycolylmannosamine.

According to other more particular embodiments, the derivative of glucosamine is N-glycolylglucosamine (GlcNGc).

According to certain embodiments, step a) is included, the derivative of glucosamine is GlcNAc, the derivative of neuraminic acid is Neu5Ac and the derivative of mannosamine is ManNAc.

According to certain embodiments, the derivative of neuraminic acid is Neu5Ac and the derivative of mannosamine is ManNAc.

According to certain embodiments, the derivative of neuraminic acid is legionaminic acid and the derivative of mannosamine is 2,4-diacetamino-2,4,6-trideoxymannose.

According to certain embodiments, the derivative of neuraminic acid is Neu5,7Ac2, Neu5,8Ac2, Neu5,9Ac2 or any mixture thereof and the derivative of mannosamine is 4-O-acetyl-2-N-acetylmannosamine, 6-O-acetyl-2-N-acetylmannosamine or any mixture thereof.

According to certain embodiments, the derivative of neuraminic acid is Neu5Gc and the derivative of mannosamine is N-glycolylmannosamine.

According to certain embodiments, the derivative of neuraminic acid is 2-keto-3-deoxy-D-glycero-D-galacto-nononic acid and the derivative of mannosamine is D-mannose.

According to particular embodiments, step a) is included, the derivative of glucosamine is GlcNAc, the derivative of neuraminic acid is Neu5Ac and the derivative of mannosamine is ManNAc.

According to particular embodiments, the derivative of neuraminic acid is Neu5Ac and the derivative of mannosamine is ManNAc.

According to particular embodiments, the derivative of neuraminic acid is legionaminic acid and the derivative of mannosamine is 2,4-diacetamino-2,4,6-trideoxymannose.

According to particular embodiments, the derivative of neuraminic acid is Neu5,7Ac2, Neu5,8Ac2, Neu5,9Ac2 or any mixture thereof and the derivative of mannosamine is 4-O-acetyl-2-N-acetylmannosamine, 6-O-acetyl-2-N-acetylmannosamine or any mixture thereof.

According to certain embodiments, step a) is included.

According to certain embodiments, the alkaline pH in step b) is in the range from about 9 to about 12, such as from about 9 to about 11.5, from about 9 to about 11, from about 9 to about 10.5, from about 9 to about 10, from about 9 to about 9.5, from about 9.5 to about 12, from about 9.5 to about 11.5, from about 9.5 to about 11, from about 9.5 to about 10.5, from about 9.5 to about 10, from about 10 to about 12, from about 10 to about 11.5, from about 10 to about 11, from about 10 to about 11, from about 10 to about 10.5, from about 10.5 to about 12, from about 10.5 to about 11.5, from about 10.5 to about 11, from about 11 to about 12, or from about 11 to about 11.5.

According to particular embodiments, the alkaline pH in step b) is in the range from about 10 to about 11.5, such as from about pH 10.5 to about 11.

According to certain embodiments, the alkaline pH in step a) is in the range from about 9 to about 12, such as from about 9 to about 11.5, from about 9 to about 11, from about 9 to about 10.5, from about 9 to about 10, from about 9 to about 9.5, from about 9.5 to about 12, from about 9.5 to about 11.5, from about 9.5 to about 11, from about 9.5 to about 10.5, from about 9.5 to about 10, from about 10 to about 12, from about 10 to about 11.5, from about 10 to about 11, from about 10 to about 11, from about 10 to about 10.5, from about 10.5 to about 12, from about 10.5 to about 11.5, from about 10.5 to about 11, from about 11 to about 12, or from about 11 to about 11.5.

According to particular embodiments, the alkaline pH in step a) is in the range from about 10 to about 11.5, such as from about pH 10.5 to about 11.

According to particular embodiments, step a) is performed at the same pH or within the same pH range as in step b).

According to certain embodiments, step b) is carried out at a temperature ranging from about 0 to about 30° C., such as from about 4 to about 30° C., from about 10 to about 30° C., from about 15 to about 30° C., from about 17 to about 30° C., from about 18 to about 30° C., from about 19 to about 30° C., from about 20 to about 30° C., from about 4 to about 25° C., from about 10 to about 25° C., from about 15 to about 25° C., from about 17 to about 25° C., from about 18 to about 25° C., from about 18.5 to about 25° C., from about 19 to about 25° C., from about 20 to about 25° C., from about 4 to about 23° C., about 10 to about 23° C., from about 15 to about 23° C., from about 17 to about 23° C., from about 18 to about 23° C., from about 19 to about 23° C., from about 20 to about 23° C., from about 4 to about 22° C., from about 10 to about 22° C., from about 15 to about 22° C., from about 17 to about 22° C., from about 18 to about 22° C., from about 19 to about 22° C., from about 20 to about 22° C., from about 4 to about 21° C., about 10 to about 21° C., from about 15 to about 21° C., from about 17 to about 21° C., from about 18 to about 21° C., or from about 19 to about 21° C.

According to certain embodiments, step a) is carried out at a temperature ranging from about 0 to about 70° C., such as from about from about 10 to about 70° C., from about 15 to about 70° C., from about 20 to about 70° C., from about 25 to about 70° C., from about 30 to about 70° C., from about 35 to about 70° C., from about 40 to about 70° C., from about 45 to about 70° C., from about 50 to about 70° C., from about 50 to about 70° C., from about 55 to about 70° C., from about 60 to about 70° C., from about 10 to 65° C., from about 15 to about 65° C., from about 20 to about 65° C., from about 25 to about 65° C., from about 30 to about 65° C., from about 35 to about 65° C., from about 40 to about 65° C., from about 45 to about 65° C., from about 50 to about 65° C., from about 55 to about 65°, from about 55 to about 65° C., from about 60 to about 65° C., from about 10 to 60° C., from about 15 to about 60° C., from about 20 to about 60° C., from about 25 to about 60° C., from about 30 to about 60° C., from about 35 to about 60° C., from about 40 to about 60° C., from about 45 to about 60° C., from about 50 to about 60° C., from about 55 to about 60° C., from about from about 10 to about 55° C., from about 15 to about 55° C., from about 20 to about 55° C., from about 25 to about 55° C., from about 30 to about 55° C., from about 35 to about 55° C., from about 40 to about 55° C., from about 45 to about 55° C., from about 50 to about 55° C., from about from about 10 to about 50° C., from about 15 to about 50° C., from about 20 to about 50° C., from about 25 to about 50° C., from about 30 to about 50° C., from about 35 to about 50° C., from about 40 to about 50° C., from about 45 to about 50° C., from about 15 to about 65° C., from about 15 to about 50° C., from about 15 to about 50° C., from about 15 to about 40° C., from about 15 to about 35° C., from about 15 to about 35° C., from about 15 to about 30° C., from about 15 to about 25° C., from about 15 to about 23° C., from about 15 to about 20° C., or from about 17 to about 23° C.

According to particular embodiments, step a) is carried out at a temperature ranging from about 45 to about 70° C., such as from about 50 to about 60° C.

According to particular embodiments, step a) is carried out at the same temperature or within the same temperature range as in step b). According to such particular embodiments, steps a) and b) may be carried out at a temperature ranging from about 15 to about 25° C., such as at about 20° C.

According to certain embodiments, the ratio of pyruvate to mannosamine or its derivative in step b) is in the range from about 1:1 to about 14:1, such as about 2:1 or about 4:1.

According to particular embodiments, the ratio of pyruvate to mannosamine or its derivative in step b) is in the range from about 2:1 to about 10:1, such as from about 2:1 to about 6:1.

According to certain embodiments, step a) and/or b) is/are carried out in CAPS buffer.

According to another aspect, the present invention provides the use of a polypeptide comprising the amino acid sequence as set forth in SEQ ID NO: 1 or a functional variant thereof in the production of neuraminic acid or a derivative thereof, such as N-acetylneuraminic acid or a derivative thereof, at an alkaline pH of at least about pH 9; wherein the functional variant is a polypeptide comprising an amino acid sequence having at least about 90% sequence identity to the amino acid sequence set forth in SEQ ID NO: 1.

According to certain embodiments, the derivative of neuraminic acid is selected from the group consisting of a) Neu5Ac; b) legionaminic acid; c) Neu5,7Ac2, Neu5,8Ac2, Neu5,9Ac2 or any mixture thereof; d) Neu5Gc; e) 2-keto-3-deoxy-D-glycero-D-galacto-nononic acid; or f) any mixture thereof.

According to particular embodiments, the derivative of neuraminic acid is selected from the group consisting of a) Neu5Ac; b) legionaminic acid; c) Neu5,7Ac2, Neu5,8Ac2, Neu5,9Ac2 or any mixture thereof; or d) any mixture thereof.

According to another aspect, the present invention provides a method for cleaving neuraminic acid or a derivative thereof, such as N-acetylneuraminic acid (Neu5Ac) or derivative thereof, the method comprises incubating neuraminic acid or a derivative thereof, such as N-acetylneuraminic acid (Neu5Ac) or a derivative thereof, in the presence of a polypeptide comprising the amino acid sequence as set forth in SEQ ID NO: 1 or a functional variant thereof; wherein the functional variant is a polypeptide comprising an amino acid sequence having at least about 90% sequence identity to the amino acid sequence set forth in SEQ ID NO: 1.

According to certain embodiments, the derivative of neuraminic acid is selected from the group consisting of a) Neu5Ac; b) legionaminic acid; c) Neu5,7Ac2, Neu5,8Ac2, Neu5,9Ac2 or any mixture thereof; d) Neu5Gc; e) 2-keto-3-deoxy-D-glycero-D-galacto-nononic acid; or f) any mixture thereof.

According to particular embodiments, the derivative of neuraminic acid is selected from the group consisting of a) Neu5Ac; b) legionaminic acid; c) Neu5,7Ac2, Neu5,8Ac2, Neu5,9Ac2 or any mixture thereof; or d) any mixture thereof.

According to another aspect, the present invention provides a method for quantitating neuraminic acid or derivative thereof in a sample, such as a biological sample, the method comprising:
a') incubating said sample in the presence of a polypeptide comprising the amino acid sequence as set forth in SEQ ID NO: 1 or a functional variant thereof; wherein the functional variant is a polypeptide comprising an amino acid sequence having at least about 90% sequence identity to the amino acid sequence set forth in SEQ ID NO: 1; and
b') determining the amount of mannosamine or a derivative thereof and/or determining the amount of pyruvate.

According to certain embodiments, the derivative of neuraminic acid is Neu5Ac and the derivative of mannosamine is ManNAc.

According to certain embodiments, the derivative of neuraminic acid is legionaminic acid and the derivative of mannosamine is 2,4-diacetamino-2,4,6-trideoxymannose.

According to certain embodiments, the derivative of neuraminic acid is Neu5,7Ac2, Neu5,8Ac2, Neu5,9Ac2 or any mixture thereof and the derivative of mannosamine is 4-O-acetyl-2-N-acetylmannosamine, 6-O-acetyl-2-N-acetylmannosamine or any mixture thereof.

According to certain embodiments, the derivative of neuraminic acid is Neu5Gc and the derivative of mannosamine is N-glycolylmannosamine.

According to certain embodiments, the derivative of neuraminic acid is 2-keto-3-deoxy-D-glycero-D-galacto-nononic acid and the derivative of mannosamine is D-mannose.

According to particular embodiments, the derivative of neuraminic acid is Neu5Ac and the derivative of mannosamine is ManNAc.

According to particular embodiments, the derivative of neuraminic acid is Neu5Gc and the derivative of mannosamine is N-glycolylmannosamine.

According to particular embodiments, the derivative of neuraminic acid is 2-keto-3-deoxy-D-glycero-D-galacto-nononic acid and the derivative of mannosamine is D-mannose.

According to another aspect, the present invention provides a method for the production of neuraminic acid or a derivative thereof comprising:
a) optionally, transforming glucosamine or a derivative thereof into mannosamine or derivative thereof by epimerization at an alkaline pH of at least about 9; and
b) reacting mannosamine or a derivative thereof with pyruvate at an alkaline pH of at least about 9 in the presence of a N-acetylneuraminate lyase from a bacterium of the Vibrionaceae family or a functional variant thereof.

The present invention also provides the use of a N-acetylneuraminate lyase from a bacterium of the Vibrionaceae family or a functional variant thereof in the production of neuraminic acid or a derivative thereof, such as N-acetylneuraminic acid (Neu5Ac) or a derivative thereof, at an alkaline pH of at least about pH 9.

The present invention also provides a method for cleaving neuraminic acid or a derivative thereof, such as N-acetylneuraminic acid (Neu5Ac) or a derivative thereof, the method comprises incubating neuraminic acid or a derivative thereof, such as N-acetylneuraminic acid (Neu5Ac) or a derivative thereof, in the presence of a N-acetylneuraminate lyase from a bacterium of the Vibrionaceae family or a functional variant thereof.

The present invention also provides a method for quantitating neuraminic acid or derivative thereof in a sample, such as a biological sample, the method comprising:
a') incubating said sample in the presence of a N-acetylneuraminate lyase from a bacterium of the Vibrionaceae family or a functional variant thereof.

According to certain embodiments, the N-acetylneuraminate lyase is from a bacterium of the genus *Aliivibrio*.

According to particular embodiments, the N-acetylneuraminate lyase is from a bacterium selected from *Aliivibrio salmonicida*, *Aliivibrio logei*, *Aliivibrio wodanis*, *Aliivibrio fischeri*, *Aliivibrio finisterrensis* or *Aliivibrio siliae*.

According to more particular embodiments, the N-acetylneuraminate lyase is from the bacterium *Aliivibrio salmonicida*.

According to certain embodiments, the bacterium is a psychrophilic bacterium.

BRIEF DESCRIPTION OF THE DRAWINGS

FIG. 12a. Production of Neu5,7Ac2/Neu5,8Ac2/Neu5,9Ac2 by asNAL by incubation of 28 μg of the enzyme with 15 mM of pyruvate and 15 mM of 4-O-acetyl-2-N-acetyl-mannosamine in 124 mM HEPES buffer at pH 8.0. Aliquots were sampled after 4.0 h. Reactions were terminated by addition of 2 μl concentrated H2SO4. The low molecular weight fractions were then derivatizated with DMB according to protocol given by the supplier. DMB-labeled sialic acids were separated by HPLC. The peaks at RT 3.56, RT 4.05 and RT4.4 correspond to Neu5,7Ac2, Neu5,8Ac2 and Neu5,9Ac2 respectively.

DETAILED DESCRIPTION OF THE INVENTION

Figure 1:
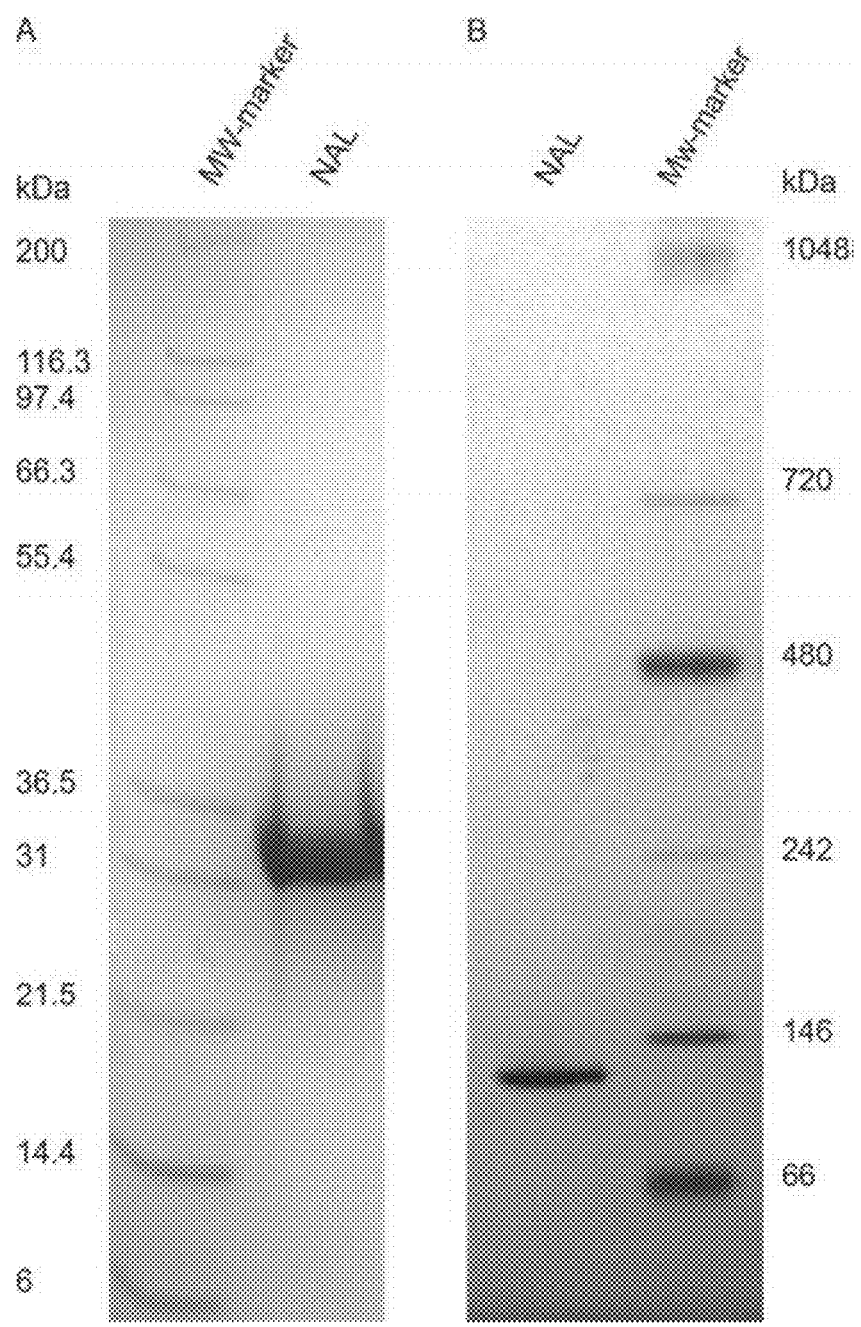
FIG. 1. SDS-PAGE of purified NAL from *A. salmonicida* (A), Lane 1: Mark12 unstained Standard (Invitrogen), Lane 2: Purified AsNAL (10.2 µg); native PAGE of AsNAL (B), Lane 1: Purified AsNAL (2.75 µg), Lane 2: NativeMark unstained protein Standard (Life technologies).

As indicated above, the present invention provides methods for the production of neuraminic acid or derivatives thereof. More particular, the present invention provides a method for the production of neuraminic acid or a derivative thereof comprising:
a) optionally, transforming glucosamine or a derivative thereof into mannosamine or a derivative thereof by epimerization at an alkaline pH of at least about 9; and
b) reacting mannosamine or a derivative thereof with pyruvate at an alkaline pH of at least about 9 in the presence of a polypeptide comprising the amino acid sequence as set forth in SEQ ID NO: 1 or a variant, such as a functional variant, thereof.

According to one aspect, the present invention provides a method for the production of neuraminic acid or a derivative thereof comprising:
a) optionally, transforming glucosamine or a derivative thereof into mannosamine or a derivative thereof by epimerization at an alkaline pH of at least about 9; and
b) reacting mannosamine or a derivative thereof with pyruvate at an alkaline pH of at least about 9 in the presence of a polypeptide comprising the amino acid sequence as set forth in SEQ ID NO: 1 or a functional variant thereof; wherein the functional variant is a polypeptide comprising an amino acid sequence having at least about 90% sequence identity to the amino acid sequence set forth in SEQ ID NO: 1.

According to certain embodiments, step a) is included, the derivative of glucosamine is GlcNAc, the derivative of neuraminic acid is Neu5Ac and the derivative of mannosamine is ManNAc.

According to certain embodiments, the derivative of neuraminic acid is Neu5Ac and the derivative of mannosamine is ManNAc.

According to certain embodiments, the derivative of neuraminic acid is legionaminic acid and the derivative of mannosamine is 2,4-diacetamino-2,4,6-trideoxymannose.

According to certain embodiments, the derivative of neuraminic acid is Neu5,7Ac2, Neu5,8Ac2, Neu5,9Ac2 or any mixture thereof and the derivative of mannosamine is 4-O-acetyl-2-N-acetylmannosamine, 6-O-acetyl-2-N-acetylmannosamine or any mixture thereof.

According to certain embodiments, the derivative of neuraminic acid is Neu5Gc and the derivative of mannosamine is N-glycolylmannosamine.

According to certain embodiments, the derivative of neuraminic acid is 2-keto-3-deoxy-D-glycero-D-galacto-nononic acid and the derivative of mannosamine is D-mannose.

According to certain embodiments, the alkaline pH in step b) is in the range from about 9 to about 12, such as from about 9 to about 11.5, from about 9 to about 11, from about 9 to about 10.5, from about 9 to about 10, from about 9 to about 9.5, from about 9.5 to about 12, from about 9.5 to about 11.5, from about 9.5 to about 11, from about 9.5 to about 10.5, from about 9.5 to about 10, from about 10 to about 12, from about 10 to about 11.5, from about 10 to about 11, from about 10 to about 11, from about 10 to about 10.5, from about 10.5 to about 12, from about 10.5 to about 11.5, from about 10.5 to about 11, from about 11 to about 12, or from about 11 to about 11.5.

According to particular embodiments, the alkaline pH in step b) is in the range from about pH 9 to about pH 11.5. According to other particular embodiments, the alkaline pH in step b) is in the range from about pH 9 to about pH 11. According to other particular embodiments, the alkaline pH in step b) is in the range from about pH 9 to about pH 10.5. According to other particular embodiments, the alkaline pH in step b) is in the range from about pH 9 to about pH 10. According to other particular embodiments, the alkaline pH in step b) is in the range from about pH 9.5 to about pH 12. According to other particular embodiments, the alkaline pH in step b) is in the range 9.5 to 11.5. According to other particular embodiments, the alkaline pH in step b) is in the range 9.5 to 11. According to other particular embodiments, the alkaline pH in step b) is in the range from about pH 9.5 to about pH 10.5. According to other particular embodiments, the alkaline pH in step b) is in the range from about pH 9.5 to about pH 10. According to other particular embodiments, the alkaline pH in step b) is in the range from about pH 10 to about pH 12. According to other particular embodiments, the alkaline pH in step b) is in the range 10 to 11.5. According to other particular embodiments, the alkaline pH in step b) is in the range 10 to 11. According to other particular embodiments, the alkaline pH in step b) is in the range from about pH 10 to about pH 10.5.

According to other particular embodiments, the alkaline pH in step b) is in the range from about pH 10.5 to about pH 12. According to other particular embodiments, the alkaline pH in step b) is in the range 10.5 to 11.5. According to other particular embodiments, the alkaline pH in step b) is in the range 10.5 to 11. According to other particular embodiments, the alkaline pH in step b) is in the range from about pH 11 to about pH 12. According to other particular embodiments, the alkaline pH in step b) is in the range from about pH 11 to about pH 11.5.

According to more particular embodiments, the alkaline pH in step b) is in the range from about pH 10 to about pH 12. According to other more particular embodiments, the alkaline pH in step b) is in the range from about pH 10.5 to about pH 11.5. Hence, the alkaline pH in step b) may be a pH of about 10, a pH of about 10.5, a pH of about 11, or a pH of about 11.5, of which a pH of about 11 and 11.5 are preferred.

According to certain embodiments, step a) is included.

According to certain embodiments, the alkaline pH in step a) is in the range from about 9 to about 12, such as from about 9 to about 11.5, from about 9 to about 11, from about 9 to about 10.5, from about 9 to about 10, from about 9 to about 9.5, from about 9.5 to about 12, from about 9.5 to about 11.5, from about 9.5 to about 11, from about 9.5 to about 10.5, from about 9.5 to about 10, from about 10 to about 12, from about 10 to about 11.5, from about 10 to about 11, from about 10 to about 11, from about 10 to about 10.5, from about 10.5 to about 12, from about 10.5 to about 11.5, from about 10.5 to about 11, from about 11 to about 12, or from about 11 to about 11.5.

According to particular embodiments, the alkaline pH in step a) is in the range from about pH 9 to about pH 11.5. According to other particular embodiments, the alkaline pH in step a) is in the range from about pH 9 to about pH 11. According to other particular embodiments, the alkaline pH in step a) is in the range from about pH 9 to about pH 10.5. According to other particular embodiments, the alkaline pH in step a) is in the range from about pH 9 to about pH 10. According to other particular embodiments, the alkaline pH in step a) is in the range from about pH 9.5 to about pH 12. According to other particular embodiments, the alkaline pH in step a) is in the range 9.5 to 11.5. According to other particular embodiments, the alkaline pH in step a) is in the range 9.5 to 11. According to other particular embodiments, the alkaline pH in step a) is in the range from about pH 9.5 to about pH 10.5. According to other particular embodiments, the alkaline pH in step a) is in the range from about pH 9.5 to about pH 10. According to other particular embodiments, the alkaline pH in step a) is in the range from about pH 10 to about pH 12. According to other particular embodiments, the alkaline pH in step a) is in the range 10 to 11.5. According to other particular embodiments, the alkaline pH in step a) is in the range 10 to 11. According to other particular embodiments, the alkaline pH in step a) is in the range from about pH 10 to about pH 10.5. According to other particular embodiments, the alkaline pH in step a) is in the range from about pH 10.5 to about pH 12. According to other particular embodiments, the alkaline pH in step a) is in the range 10.5 to 11.5. According to other particular embodiments, the alkaline pH in step a) is in the range 10.5 to 11. According to other particular embodiments, the alkaline pH in step a) is in the range from about pH 11 to about pH 12. According to other particular embodiments, the alkaline pH in step a) is in the range from about pH 11 to about pH 11.5.

According to more particular embodiments, the alkaline pH in step a) is in the range from about pH 10 to about pH 12. According to other more particular embodiments, the alkaline pH in step a) is in the range from about pH 10.5 to about pH 11.5. Hence, the alkaline pH in step a) may be a pH of about 10, a pH of about 10.5, a pH of about 11, or a pH of about 11.5, of which a pH of about 11 and 11.5 are preferred.

According to particular embodiments, step a) is carried out at the same pH or within the same pH range as in step b). Therefore, steps a) and b) may be carried out at a pH in the range from about pH 9 to about pH 12, such as from about pH 10 to about pH 12 or from about pH 10.5 to about pH 11.5. For example, steps a) and b) may both be carried out at a pH of about 11. Steps a) and b) may both also be carried out at a pH of about 11.5.

In order to obtain the desired pH, any buffering agent suitable for maintaining such pH known in the art may be used. Suitable buffering agents for use according to the invention include, but are not limited to, CAPS (N-cyclohexyl-3-aminopropanesulfonic acid), CHES (N-Cyclohexyl-2-aminoethanesulfonic acid), Glycine, sodium bicarbonate/sodium hydroxide, and sodium hydrogen orthophosphate/sodium hydroxide. The skilled person is aware of appropriate amounts of the respective buffering agent to be employed.

According to certain embodiments, step a) and/or b) are carried out at a temperature in the range from about 0 to about 70° C., such as from about 4 to about 65° C., from about 10 to about 65° C., from about 15 to about 65° C., from about 20 to about 65° C., from about 4 to about 60° C., from about 10 to about 60° C., from about 15 to about 60° C., from about 20 to about 60° C., from about 4 to about 55° C., from about 10 to 55° C., from about 15 to about 55° C., from about 20 to about 55° C., from about 4 to about 50° C., from about 10 to about 50° C., from about 15 to about 50° C., from about 20 to about 50° C., such as from about 4 to about 45° C., from about 10 to about 45° C., from about 15 to about 45° C., from about 20 to about 45° C., such as from about 4 to about 40° C., from about 10 to about 40° C., from about 15 to about 40° C., from about 20 to about 40° C., such as from about 4 to about 35° C., from about 10 to about 35° C., from about 15 to about 35° C., from about 20 to about 35° C., such as from about 4 to about 30° C., from about 10 to about 30° C., from about 15 to about 30° C., from about 20 to about 30° C., such as from about 4 to about 25° C., from about 10 to about 25° C., from about 15 to about 25° C., from about 20 to about 25° C., such as from about 4 to about 23° C., from about 10 to about 23° C., from about 15 to about 23° C., from about 17 to about 23° C., or from about 20 to about 23° C.

According to certain embodiments, step a) and/or b) are carried at room temperature.

According to particular embodiments, step b) is carried out at a temperature ranging from about 0 to about 30° C. According to more particular embodiments, step b) is carried out at a temperature ranging from about 4 to about 30° C. According to other more particular embodiments step b) is carried out at a temperature ranging from about 10 to about 30° C. According to other more particular embodiments step b) is carried out at a temperature ranging from about 15 to about 30° C. According to other more particular embodiments step b) is carried out at a temperature ranging from about 17 to about 30° C. According to other more particular embodiments step b) is carried out at a temperature ranging from about 18 to about 30° C. According to other more particular embodiments step b) is carried out at a temperature ranging from about 19 to about 30° C. According to other more particular embodiments step b) is carried out at a temperature ranging from about 20 to about 30° C. According to other more particular embodiments step b) is carried out at a temperature ranging from about 4 to about 25° C. According to other more particular embodiments step b) is carried out at a temperature ranging from about 10 to about 25° C. According to other more particular embodiments step b) is carried out at a temperature ranging from about 15 to about 25° C. According to other more particular embodiments step b) is carried out at a temperature ranging from about 17 to about 25° C. According to other more particular embodiments step b) is carried out at a temperature ranging from about 18 to about 25° C.

According to other more particular embodiments step b) is carried out at a temperature ranging from about 19 to about 25° C. According to other more particular embodiments step b) is carried out at a temperature ranging from about 20 to about 25° C. According to other more particular embodiments step b) is carried out at a temperature ranging from about 4 to about 23° C. According to other more particular embodiments step b) is carried out at a temperature ranging about 10 to about 23° C. According to other more particular embodiments step b) is carried out at a temperature ranging from about 15 to about 23° C. According to other more particular embodiments step b) is carried out at a temperature ranging from about 17 to about 23° C. According to other more particular embodiments step b) is carried out at a temperature ranging from about 18 to about 23° C. According to other more particular embodiments step b) is carried out at a temperature ranging from about 19 to about 23° C. According to other more particular embodiments step b) is carried out at a temperature ranging from about 20 to about 23° C. According to other more particular embodiments step b) is carried out at a temperature ranging from about 4 to about 22° C. According to other more particular embodiments step b) is carried out at a temperature ranging from about 10 to about 22° C. According to other more particular embodiments step b) is carried out at a temperature ranging from about 15 to about 22° C. According to other more particular embodiments step b) is carried out at a temperature ranging from about 17 to about 22° C. According to other more particular embodiments step b) is carried out at a temperature ranging from about 18 to about 22° C. According to other more particular embodiments step b) is carried out at a temperature ranging from about 19 to about 22° C.

According to other more particular embodiments step b) is carried out at a temperature ranging from about 20 to about 22° C. According to other more particular embodiments step b) is carried out at a temperature ranging from about 4 to about 21° C. According to other more particular embodiments step b) is carried out at a temperature ranging from about 10 to about 21° C. According to other more particular embodiments step b) is carried out at a temperature ranging from about 15 to about 21° C. According to other more particular embodiments step b) is carried out at a temperature ranging from about 17 to about 21° C. According to other more particular embodiments step b) is carried out at a temperature ranging from about 18 to about 21° C. According to other more particular embodiments step b) is carried out at a temperature ranging or from about 19 to about 21° C.

For example, step b) may be carried out at about 20° C.

According to particular embodiments, step a) is performed at a temperature in the range from about 0 to about 70° C., such as from about 40 to about 70° C. According to more particular embodiments, step a) is carried out at a temperature ranging from about 45 to about 65° C. According to other more particular embodiments, step a) is carried out at a temperature ranging from about 45 to about 65° C. According to other more particular embodiments, step a) is carried out at a temperature ranging from about 50 to about 65° C. According to other more particular embodiments, step a) is carried out at a temperature ranging from about 55 to about 65° C. According to other more particular embodiments, step a) is carried out at a temperature ranging from about 45 to about 60° C. According to other more particular embodiments, step a) is carried out at a temperature ranging from about 50 to about 60° C.

According to other particular embodiments, step a) is carried out at a temperature ranging from about 0 to about 30° C. such as from about 15 to about 25° C. According to more particular embodiments, step a) is carried out at a temperature ranging from about 17 to about 25° C. According to other more particular embodiments step a) is carried out at a temperature ranging from about 18 to about 25° C. According to other more particular embodiments step a) is carried out at a temperature ranging from about 19 to about 25° C. According to other more particular embodiments step a) is carried out at a temperature ranging from about 20 to about 25° C. According to other more particular embodiments, step a) is carried out at a temperature ranging from about 15 to about 23° C. According to other more particular embodiments step a) is carried out at a temperature ranging from about 17 to about 23° C. According to other more particular embodiments step a) is carried out at a temperature ranging from about 18 to about 23° C. According to other more particular embodiments step a) is carried out at a temperature ranging from about 19 to about 23° C.

According to other more particular embodiments step a) is carried out at a temperature ranging from about 20 to about 23° C. According to other more particular embodiments step a) is carried out at a temperature ranging from about 15 to about 22° C. According to other more particular embodiments step a) is carried out at a temperature ranging from about 17 to about 22° C. According to other more particular embodiments step a) is carried out at a temperature ranging from about 18 to about 22° C. According to other more particular embodiments step a) is carried out at a temperature ranging from about 19 to about 22° C. According to other more particular embodiments step a) is carried out at a temperature ranging from about 20 to about 22° C. According to other more particular embodiments step a) is carried out at a temperature ranging from about 15 to about 21° C. According to other more particular embodiments step a) is carried out at a temperature ranging from about 17 to about 21° C. According to other more particular embodiments step a) is carried out at a temperature ranging from about 18 to about 21° C. According to other more particular embodiments step a) is carried out at a temperature ranging or from about 19 to about 21° C.

For example, step a) may be carried out at about 20° C.

According to certain embodiments, step a) is carried out at the same temperature or within the same temperature range as in step b). For example, steps a) and b) may be are carried out at a temperature ranging from about 15 to about 25° C. According to particular embodiments, steps a) and b) are carried out at a temperature ranging from about 17 to about 23° C. According to more particular embodiments, steps a) and b) are carried out at a temperature ranging from about 18 to about 22° C.

For example, steps a) and b) may be carried out at about 20° C.

According to certain embodiments, the ratio of pyruvate to mannosamine (or derivative thereof) in step b) is in the range from about 1:1 to about 14:1. According to particular embodiments, the ratio of pyruvate to mannosamine (or derivative thereof) in step b) is in the range from about 2:1 to about 14:1. According to other particular embodiments, the ratio of pyruvate to mannosamine (or derivative thereof) in step b) is in the range from about 4:1 to about 14:1. According to other particular embodiments, the ratio of pyruvate to mannosamine (or derivative thereof) in step b) is in the range from about 2:1 to about 10:1.

According to other particular embodiments, the ratio of pyruvate to mannosamine (or derivative thereof) in step b) is in the range from about 2:1 to about 8:1. According to other particular embodiments, the ratio of pyruvate to mannosamine (or derivative thereof) in step b) is in the range from about 2:1 to about 6:1. According to other particular embodiments, the ratio of pyruvate to mannosamine (or derivative thereof) in step b) is in the range from about 4:1 to about 10:1. According to other particular embodiments, the ratio of pyruvate to mannosamine (or derivative thereof) in step b) is in the range from about 4:1 to about 8:1. According to other particular embodiments, the ratio of pyruvate to mannosamine (or derivative thereof) in step b) is in the range from about 4:1 to about 6:1, such as about 5:1. According to other particular embodiments, the ratio of pyruvate to mannosamine (or derivative thereof) in step b) is in the range from about 3:1 to about 5:1. According to more particular embodiments, the ratio of pyruvate to mannosamine (or derivative thereof) in step b) is about 2:1. According to other more particular embodiments, the ratio of pyruvate to mannosamine (or derivative thereof) in step b) is about 4:1.

Generally, steps a) and b) may be carried out until the respective reaction is completed. For example, step b) may be carried out for a time period of at least about 4 hours, such as at least about 12 hours or at least about 24 hours. Therefore, according to certain embodiments, step b) is carried out for at least about 4 hours. According to other certain embodiments, step b) is carried out for at least about 5 hours. According to other certain embodiments, step b) is carried out for at least about 6 hours. According to other certain embodiments, step b) is carried out for at least about 7 hours. According to other certain embodiments, step b) is carried out for at least about 8 hours. According to other certain embodiments, step b) is carried out for at least about 9 hours. According to other certain embodiments, step b) is carried out for at least about 10 hours. According to other certain embodiments, step b) is carried out for at least about 11 hours. According to other certain embodiments, step b) is carried out for at least about 12 hours. According to other certain embodiments, step b) is carried out for at least about 18 hours. According to other certain embodiments, step b) is carried out for at least about 24 hours. According to other certain embodiments, step b) is carried out for at least about 36 hours. According to other certain embodiments, step b) is carried out for at least about 48 hours. According to other certain embodiments, step b) is carried out for at least about 60 hours. According to other certain embodiments, step b) is carried out for at least about 72 hours.

For example, step b) may be carried out for a time period of at the most about 72 hours, such as at the most about 48 hours or at the most about 24 hours. Therefore, according to certain embodiments, step b) is carried out for at the most about 72 hours. According to other certain embodiments, step b) is carried out for at the most about 60 hours. According to other certain embodiments, step b) is carried out for at the most about 48 hours. According to other certain embodiments, step b) is carried out for at the most about 36 hours. According to other certain embodiments, step b) is carried out for at the most about 24 hours. According to other certain embodiments, step b) is carried out for at the most about 18 hours. According to other certain embodiments, step b) is carried out for at the most about 12 hours. According to other certain embodiments, step b) is carried out for at the most about 11 hours. According to other certain embodiments, step b) is carried out for at the most about 10 hours. According to other certain embodiments, step b) is carried out for at the most about 9 hours. According to other certain embodiments, step b) is carried out for at the most about 8 hours. According to other certain embodiments, step b) is carried out for at the most about 7 hours. According to other certain embodiments, step b) is carried out for at the most about 6 hours. According to other certain embodiments, step b) is carried out for at the most about 5 hours. According to other certain embodiments, step b) is carried out for at the most about 4 hours.

Step a) may, for instance, be carried out for a time period of at least about 4 hours, such as at least about 8 hours or at least about 12 hours. Therefore, according to certain embodiments, step a) is carried out for at least about 4 hours. According to other certain embodiments, step a) is carried out for at least about 8 hours. According to other certain embodiments, step a) is carried out for at least about 12 hours. According to other certain embodiments, step a) is carried out for at least about 18 hours. According to other certain embodiments, step a) is carried out for at least about 24 hours. According to other certain embodiments, step a) is carried out for at least about 36 hours. According to other certain embodiments, step a) is carried out for at least about 48 hours. According to other certain embodiments, step a) is carried out for at least about 72 hours.

Step a) may, for instance, be carried out for a time period of at the most about 72 hours, such as at the most about 48 hours or at the most about 24 hours. Therefore, according to certain embodiments, step a) is carried out for at the most about 72 hours. According to other certain embodiments, step a) is carried out for at the most about 60 hours. According to other certain embodiments, step a) is carried out for at the most about 48 hours.

According to other certain embodiments, step a) is carried out for at the most about 36 hours. According to other certain embodiments, step a) is carried out for at the most about 24 hours. According to other certain embodiments, step a) is carried out for at the most about 18 hours. According to other certain embodiments, step a) is carried out for at the most about 12 hours.

According to certain embodiments, the method comprises:
- a1) transforming glucosamine or a derivative thereof (such as N-acetylglycosamine) into mannosamine or derivative thereof (such as N-acetylmannosamine) by epimerization at an alkaline pH of at least about 9 and at a temperature ranging from about 40 to about 70° C., such as from about 50° to about 60° C.;
- a2) reducing the temperature to about 0 to about 30° C., such as to about 15 to about 25° C.;
- b1) adding pyruvate and a polypeptide comprising the amino acid sequence as set forth in SEQ ID NO: 1 or a variant, such as a functional variant, thereof; and
- b2) reacting mannosamine or a derivative thereof (such as N-acetylmannosamine) with pyruvate at an alkaline pH of at least about 9 and at a temperature ranging from about 0 to about 30° C., such as to about 15 to about 25° C., in the presence of said polypeptide or variant thereof.

According to particular embodiments, the alkaline pH in step a1) is in the range from about 9 to about 12, such as from about 9.5 to about 11.5. According to more particular embodiments, the alkaline pH in step a1) is in the range from about 10.5 to about 11.5.

According to particular embodiments, the alkaline pH in step b2) is in the range from about 9 to about 12, such as from about 9.5 to about 11.5. According to more particular embodiments, the alkaline pH in step b2) is in the range from about 10.5 to about 11.5.

According to particular embodiments, step a1) is carried out at a temperature ranging from about 45 to about 65° C. According to more particular embodiments, step a1) is carried out at a temperature ranging from about 50 to about 65° C. According to other more particular embodiments, step a1) is carried out at a temperature ranging from about 55 to about 65° C. According to other more particular embodiments, step a1) is carried out at a temperature ranging from about 45 to about 60° C. According to other more particular embodiments, step a1) is carried out at a temperature ranging from about 50 to about 60° C.

According to particular embodiments, step b2) is carried out at a temperature ranging from about 4 to about 25° C. According to more particular embodiments, step b2) is carried out at a temperature ranging from about 10 to about 25° C. According to other more particular embodiments, step b2) is carried out at a temperature ranging from about 15 to about 25° C. According to other more particular embodiments, step b2) is carried out at a temperature ranging from about 15 to about 23° C. According to other more particular embodiments, step b2) is carried out at a temperature ranging from about 17 to about 23° C. According to other more particular embodiments, step b2) is carried out at a temperature ranging from about 18 to about 22° C. According to other more particular embodiments, step b2) is carried out at a temperature ranging or from about 19 to about 21° C. For example, step b2) may be carried out at about 20° C.

According to particular embodiments, step a1) may be carried out for a time period of at least about 4 hours, such as at least about 12 hours.

According to particular embodiments, step b2) may be carried out for a time period of at least about 4 hours, such as at least about 12 hours.

According to certain embodiments, the ratio of pyruvate to mannosamine (or derivative thereof) in step b2) is in the range from about 1:1 to about 14:1. According to particular embodiments, the ratio of pyruvate to mannosamine (or derivative thereof) in step b2) is in the range from about 2:1 to about 14:1. According to other particular embodiments, the ratio of pyruvate to mannosamine (or derivative thereof) in step b2) is in the range from about 4:1 to about 14:1. According to other particular embodiments, the ratio of pyruvate to mannosamine (or derivative thereof) in step b2) is in the range from about 2:1 to about 10:1. According to other particular embodiments, the ratio of pyruvate to mannosamine (or derivative thereof) in step b2) is in the range from about 2:1 to about 8:1. According to other particular embodiments, the ratio of pyruvate to mannosamine (or derivative thereof) in step b2) is in the range from about 4:1 to about 10:1. According to other particular embodiments, the ratio of pyruvate to mannosamine (or derivative thereof) in step b2) is in the range from about 4:1 to about 8:1. According to other particular embodiments, the ratio of pyruvate to mannosamine (or derivative thereof) in step b2) is in the range from about 4:1 to about 6:1, such as about 5:1. According to other particular embodiments, the ratio of pyruvate to mannosamine (or derivative thereof) in step b2) is in the range from about 3:1 to about 5:1.

According to more particular embodiments, the ratio of pyruvate to mannosamine (or derivative thereof) in step b2) is about 2:1. According to other more particular embodiments, the ratio of pyruvate to mannosamine (or derivative thereof) in step b2) is about 4:1.

Since the polypeptides employed in accordance with the invention are suitable to catalyze the formation of neuraminic acid or derivative thereof from mannosamine or derivative thereof and pyruvate under alkaline conditions, the method of the present invention may involve integrated reaction condition(s) which means that a mixture of glucosamine or derivative thereof, pyruvate and the polypeptide is incubated at an alkaline pH of at least about 9. Under this condition glucosamine or said derivative thereof is epimerized into mannosamine or respective derivative thereof which is immediately converted by the polypeptide into neuraminic acid or respective derivative thereof in the presence of pyruvate. In other words, the present invention allows the direct conversion of the glucosamine or derivative thereof as starting material into neuraminic acid or respective derivative thereof without the use of an epimerase.

Accordingly, a method for the production of neuraminic acid or a derivative thereof as detailed herein may comprise:

Incubating a mixture of glucosamine or a derivative thereof, pyruvate and a polypeptide comprising the amino acid sequence as set forth in SEQ ID NO: 1 or a variant, such as a functional variant, thereof at an alkaline pH of at least about 9.

According to certain embodiments, the mixture is incubated at a temperature ranging from about 0 to about 30° C., such as from about 4 to about 25° C. According to particular embodiments, the mixture is incubated at a temperature ranging from about 10 to about 25° C. According to more particular embodiments, the mixture is incubated at a temperature ranging from about 15 to about 25° C. According to other more particular embodiments the mixture is incubated at a temperature ranging from about 18 to about 25° C. According to other more particular embodiments the mixture is incubated at a temperature ranging from about 19 to about 25° C. According to other more particular embodiments the mixture is incubated at a temperature ranging from about 20 to about 25° C. According to other more particular embodiments, the mixture is incubated at a temperature ranging from about 15 to about 23° C. According to other more particular embodiments the mixture is incubated at a temperature ranging from about 17 to about 23° C. According to other more particular embodiments the mixture is incubated at a temperature ranging from about 18 to about 23° C. According to other more particular embodiments, the mixture is incubated at a temperature ranging from about 19 to about 23° C. According to other more particular embodiments, the mixture is incubated at a temperature ranging from about 20 to about 23° C. According to other more particular embodiments, the mixture is incubated at a temperature ranging from about 15 to about 22° C. According to other more particular embodiments, the mixture is incubated at a temperature ranging from about 17 to about 22° C. According to other more particular embodiments, the mixture is incubated at a temperature ranging from about 18 to about 22° C. According to other more particular embodiments, the mixture is incubated at a temperature ranging from about 19 to about 22° C. According to other more particular embodiments, the mixture is incubated at a temperature ranging from about 20 to about 22° C. According to other more particular embodiments, the mixture is incubated at a temperature ranging from about 15 to about 21° C. According to other more particular embodiments, the mixture is incubated at a temperature ranging from about 17 to about 21° C. According to other more particular embodiments the mixture is incubated at a temperature ranging from about 18 to about 21° C. According to other more particular embodiments, the mixture is incubated at a temperature ranging from about 19 to about 21° C.

For example, the mixture may be incubated at about 20° C.

The incubation may take as long as it takes for completely converting N-acetylglucosamine into N-acetylneuraminic acid. However, according to certain embodiments, the mixture is incubated for a time period of at least about 6 hours. According to certain other embodiments, the mixture is incubated for a time period of at least about 12 hours. According to certain other embodiments, the mixture is incubated for a time period of at least about 48 hours. According to certain other embodiments, the mixture is incubated for a time period of at least about 36 hours. According to certain other embodiments, the mixture is incubated for a time period of at least about 24 hours. According to certain other embodiments, the mixture is incubated for a time period of at least about 36 hours. According to certain other embodiments, the mixture is incubated for a time period of at least about 48 hours.

For example, the mixture may be incubated for a time period of at the most 96 hours. According to certain other embodiments, the mixture is incubated for a time period of at the most about 72 hours. According to certain other embodiments, the mixture is incubated for a time period of at the most about 60 hours.

According to certain other embodiments, the mixture is incubated for a time period of at the most about 60 hours. According to certain other embodiments, the mixture is incubated for a time period of at the most about 48 hours. According to certain other embodiments, the mixture is incubated for a time period of at the most about 36 hours. According to certain other embodiments, the mixture is incubated for a time period of at the most about 24 hours. According to certain other embodiments, the mixture is incubated for a time period of at the most about 18 hours. According to certain other embodiments, the mixture is incubated for a time period of at the most about 12 hours.

According to certain embodiments, the mixture is incubated for a time period in the range from about 12 to about 72 hours. According to certain other embodiments, the mixture is incubated for a time period in the range from about 12 to about 60 hours. According to certain other embodiments, the mixture is incubated for a time period in the range from about 12 to about 48 hours. According to certain other embodiments, the mixture is incubated for a time period in the range from about 12 to about 36 hours.

According to certain embodiments, the ratio of pyruvate to glucosamine (or derivative thereof) is in the range from about 1:1 to about 14:1. According to particular embodiments, the ratio of pyruvate to glucosamine (or derivative thereof) is in the range from about 2:1 to about 14:1. According to other particular embodiments, the ratio of pyruvate to glucosamine (or derivative thereof) is in the range from about 4:1 to about 14:1. According to other particular embodiments, the ratio of pyruvate to glucosamine (or derivative thereof) is in the range from about 2:1 to about 10:1. According to other particular embodiments, the ratio of pyruvate to glucosamine (or derivative thereof) is in the range from about 2:1 to about 6:1. According to other particular embodiments, the ratio of pyruvate to glucosamine (or derivative thereof) in step b) is in the range from about 2:1 to about 8:1. According to other particular embodiments, the ratio of pyruvate to glucosamine (or derivative thereof) is in the range from about 4:1 to about 10:1. According to other particular embodiments, the ratio of pyruvate to glucosamine (or derivative thereof) is in the range from about 4:1 to about 8:1. According to other particular embodiments, the ratio of pyruvate to glucosamine (or derivative thereof) is in the range from about 4:1 to about 6:1, such as about 5:1. According to other particular embodiments, the ratio of pyruvate glucosamine (or derivative thereof) is in the range from about 3:1 to about 5:1. According to more particular embodiments, the ratio of pyruvate to glucosamine (or derivative thereof) is about 2:1. According to more particular embodiments, the ratio of pyruvate to glucosamine (or derivative thereof) is about 4:1.

The present invention also provides the use of a polypeptide comprising the amino acid sequence as set forth in SEQ ID NO: 1 or a functional variant thereof in the production of neuraminic acid (Neu5Ac) or a derivative thereof, such as N-acetylneuraminic acid (Neu5Ac) or derivative thereof, at an alkaline pH of at least about pH 9. It is understood that details given above, in particular with respect to certain condition such as pH, temperature, ratios, timing etc., apply mutatis mutandis to this aspect of the invention.

According to another aspect, the present invention provides the use of a polypeptide comprising the amino acid sequence as set forth in SEQ ID NO: 1 or a functional variant thereof in the production of neuraminic acid (Neu5Ac) or a derivative thereof, such as N-acetylneuraminic acid (Neu5Ac) or derivative thereof, at an alkaline pH of at least about pH 9; wherein the functional variant is a polypeptide comprising an amino acid sequence having at least about 90% sequence identity to the amino acid sequence set forth in SEQ ID NO: 1.

According to certain embodiments, the derivative of neuraminic acid is selected from the group consisting of a) Neu5Ac; b) legionaminic acid; c) Neu5,7Ac2, Neu5,8Ac2, Neu5,9Ac2 or any mixture thereof; d) Neu5Gc; e) 2-keto-3-deoxy-D-glycero-D-galacto-nononic acid; or f) any mixture thereof.

According to certain embodiments, the derivative of neuraminic acid is selected from the group consisting of a) Neu5Ac; b) legionaminic acid; c) Neu5,7Ac2, Neu5,8Ac2, Neu5,9Ac2 or any mixture thereof; or d) any mixture thereof.

It is understood that details given above, in particular with respect to certain condition such as pH, temperature, ratios, timing etc., apply mutatis mutandis to this aspect of the invention.

The present invention also provides a method for the production of neuraminic acid or a derivative thereof comprising:

a) optionally, transforming glucosamine or a derivative thereof into mannosamine (ManNAc) or derivative thereof by epimerization at an alkaline pH of at least about 9; and
b) reacting mannosamine or a derivative thereof with pyruvate at an alkaline pH of at least about 9 in the presence of a N-acetylneuraminate lyase from a bacterium of the Vibrionaceae family or a functional variant thereof.

It is understood that details given above, in particular with respect to certain condition such as pH, temperature, ratios etc., apply mutatis mutandis to this aspect of the invention.

According to certain embodiments, the N-acetylneuraminate lyase is from a bacterium of the genus *Aliivibrio*.

According to particular embodiments, the N-acetylneuraminate lyase is from a bacterium selected from *Aliivibrio salmonicida, Aliivibrio logei, Aliivibrio wodanis, Aliivibrio fischeri, Aliivibrio finisterrensis* or *Aliivibrio siliae*.

According to more particular embodiments, the N-acetylneuraminate lyase is from the bacterium *Aliivibrio salmonicida*.

According to certain embodiments, the bacterium is a psychrophilic bacterium.

The present invention also provides the use of a N-acetylneuraminate lyase from a bacterium of the Vibrionaceae family or a functional variant thereof in the production of neuraminic acid or a derivative, such as N-acetylneuraminic acid (Neu5Ac) or derivative thereof, thereof at an alkaline pH of at least about pH 9.

It is understood that details given above, in particular with respect to certain condition such as pH, temperature, ratios etc., apply mutatis mutandis to this aspect of the invention.

According to certain embodiments, the N-acetylneuraminate lyase is from a bacterium of the genus *Aliivibrio*.

According to particular embodiments, the N-acetylneuraminate lyase is from a bacterium selected from *Aliivibrio salmonicida, Aliivibrio logei, Aliivibrio wodanis, Aliivibrio fischeri, Aliivibrio finisterrensis* or *Aliivibrio siliae*.

According to more particular embodiments, the N-acetylneuraminate lyase is from the bacterium *Aliivibrio salmonicida*.

According to certain embodiments, the bacterium is a psychrophilic bacterium.

The present invention also provides a method for cleaving neuraminic acid or a derivative thereof, such as N-acetylneuraminic acid (Neu5Ac) or a derivative thereof, the method comprises incubating neuraminic acid in the presence of a polypeptide comprising the amino acid sequence as set forth in SEQ ID NO: 1 or a functional variant thereof.

According to another aspect, the present invention provides a method for cleaving neuraminic acid or a derivative thereof, such as N-acetylneuraminic acid (Neu5Ac) or a derivative thereof, the method comprises incubating neuraminic acid in the presence of a polypeptide comprising the amino acid sequence as set forth in SEQ ID NO: 1 or a functional variant thereof; wherein the functional variant is a polypeptide comprising an amino acid sequence having at least about 90% sequence identity to the amino acid sequence set forth in SEQ ID NO: 1.

According to certain embodiments, the derivative of neuraminic acid is selected from the group consisting of a) Neu5Ac; b) legionaminic acid; c) Neu5,7Ac2, Neu5,8Ac2, Neu5,9Ac2 or any mixture thereof; d) Neu5Gc; e) 2-keto-3-deoxy-D-glycero-D-galacto-nononic acid; or f) any mixture thereof.

According to certain embodiments, the derivative of neuraminic acid is selected from the group consisting of a) Neu5Ac; b) Neu5Gc; c) 2-keto-3-deoxy-D-glycero-D-galacto-nononic acid; or d) any mixture thereof.

According to certain embodiments, incubation is carried out at a temperature ranging from about 0 to about 30° C., such as from about 4 to about 25° C. According to particular embodiments, incubation is carried out at a temperature ranging from about 10 to about 25° C. According to more particular embodiments, incubation is carried out at a temperature ranging from about 15 to about 25° C. According to other more particular embodiments, incubation is carried out at a temperature ranging from about 18 to about 25° C. According to other more particular embodiments, incubation is carried out at a temperature ranging from about 19 to about 25° C. According to other more particular embodiments, incubation is carried out at a temperature ranging from about 20 to about 25° C. According to other more particular embodiments, incubation is carried out at a temperature ranging from about 15 to about 23° C. According to other more particular embodiments, incubation is carried out at a temperature ranging from about 17 to about 23° C. According to other more particular embodiments, incubation is carried out at a temperature ranging from about 18 to about 23° C. According to other more particular embodiments, incubation is carried out at a temperature ranging from about 19 to about 23° C. According to other more particular embodiments, incubation is carried out at a temperature ranging from about 20 to about 23° C. According to other more particular embodiments, incubation is carried out at a temperature ranging from about 15 to about 22° C. According to other more particular embodiments, incubation is carried out at a temperature ranging from about 17 to about 22° C. According to other more particular embodiments, incubation is carried out at a temperature ranging from about 18 to about 22° C. According to other more particular embodiments, incubation is carried out at a temperature ranging from about 19 to about 22° C. According to other more particular embodiments, incubation is carried out at a temperature ranging from about 20 to about 22° C. According to other more particular embodiments, incubation is carried out at a temperature ranging from about 15 to about 21° C. According to other more particular embodiments, incubation is carried out at a temperature ranging from about 17 to about 21° C. According to other more particular embodiments, incubation is carried out at a temperature ranging from about 18 to about 21° C. According to other more particular embodiments, incubation is carried out at a temperature ranging from about 19 to about 21° C.

For example, the incubation may be carried out at about 20° C.

According to certain other embodiments, incubation is carried out at a temperature ranging from about 30 to about 80° C., such as from about 50 to about 70° C. According to particular embodiments, incubation is carried out at a temperature ranging from about 60 to about 70° C., such as from about 62 to about 68° C. According to more particular embodiments, incubation is carried out at a temperature ranging from about 63 to about 67° C., such as from about 64 to about 66° C. For example, incubation may be carried out at about 65° C.

The incubation may take as long as it takes for completely cleaving neuraminic acid. However, according to certain embodiments, incubation is carried out for a time period of at least about 6 hours. According to certain other embodiments, incubation is carried out for a time period of at least about 12 hours. According to certain other embodiments, incubation is carried out for a time period of at least about 48 hours. According to certain other embodiments, incubation is carried out for a time period of at least about 36 hours. According to certain other embodiments, incubation is carried out for a time period of at least about 24 hours. According to certain other embodiments, incubation is carried out for a time period of at least about 36 hours. According to certain other embodiments, incubation is carried out for a time period of at least about 48 hours. According to certain other embodiments, incubation is carried out for a time period of at least about 60 hours. According to certain other embodiments, incubation is carried out for a time period of at least about 72 hours.

For example, incubation may be carried out for a time period of at the most 96 hours.

According to certain other embodiments, incubation is carried out for a time period of at the most about 72 hours. According to certain other embodiments, incubation is carried out for a time period of at the most about 60 hours. According to certain other embodiments, incubation is carried out for a time period of at the most about 48 hours. According to certain other embodiments, incubation is carried out for a time period of at the most about 24 hours.

According to certain other embodiments, incubation is carried out for a time period of at the most about 12 hours.

According to certain embodiments, incubation is carried out at a pH ranging from about 7 to about 9, such as from about 7.5 to about 8.5. According to particular embodiments, incubation is carried out at a pH ranging from about 8 to about 9, such as from about 8 to about 8.5.

In order to obtain the desired pH, any suitable buffering agent suitable for maintaining such pH known in the art may be used. Suitable buffering agents for use according to this aspect include, but are not limited to, Tris (2-Amino-2-(hydroxymethyl)-propan-1,3-diol), HEPES (4-(2-hydroxyethyl)-1-piperazineethanesulfonic acid), triethanolamine, MOPS, MOBS and DIPSO. The skilled person is aware of appropriate amounts of the respective buffering agent to be employed.

According to another aspect, the present invention provides a method for cleaving neuraminic acid or a derivative thereof, the method comprises incubating neuraminic acid or a derivative thereof in the presence of a N-acetylneuraminate lyase from a bacterium of the Vibrionaceae family or a functional variant thereof. It is understood that details given in the context of the foregoing aspect, in particular with respect to certain condition such as pH, temperature, timing etc., apply mutatis mutandis to this aspect of the invention.

According to certain embodiments, the N-acetylneuraminate lyase is from a bacterium of the genus *Aliivibrio*.

According to particular embodiments, the N-acetylneuraminate lyase is from a bacterium selected from *Aliivibrio salmonicida, Aliivibrio logei, Aliivibrio wodanis, Aliivibrio fischeri, Aliivibrio finisterrensis* or *Aliivibrio siliae*.

According to more particular embodiments, the N-acetylneuraminate lyase is from the bacterium *Aliivibrio salmonicida*.

According to certain embodiments, the bacterium is a psychrophilic bacterium.

The present invention provides a method for quantitating neuraminic acid or derivative thereof, such as N-acetylneuraminic acid (Neu5Ac), in a sample, such as a biological sample, the method comprising:
  a') incubating said sample in the presence of a polypeptide comprising the amino acid sequence as set forth in SEQ ID NO: 1 or a functional variant thereof.

According to another aspect, the present invention provides a method for quantitating neuraminic acid or derivative thereof, such as N-acetylneuraminic acid (Neu5Ac), in a sample, such as a biological sample, the method comprising:
  a') incubating said sample in the presence of a polypeptide comprising the amino acid sequence as set forth in SEQ ID NO: 1 or a functional variant thereof; wherein the functional variant is a polypeptide comprising an amino acid sequence having at least about 90% sequence identity to the amino acid sequence set forth in SEQ ID NO: 1; and
  b') determining the amount of mannosamine or a derivative thereof and/or determining the amount of pyruvate.

According to certain embodiments, the derivative of neuraminic acid is Neu5Ac and the derivative of mannosamine is ManNAc.

According to certain embodiments, the derivative of neuraminic acid is legionaminic acid and the derivative of mannosamine is 2,4-diacetamino-2,4,6-trideoxymannose.

According to certain embodiments, the derivative of neuraminic acid is Neu5,7Ac2, Neu5,8Ac2, Neu5,9Ac2 or any mixture thereof and the derivative of mannosamine is 4-O-acetyl-2-N-acetylmannosamine, 6-O-acetyl-2-N-acetylmannosamine or any mixture thereof;

According to certain embodiments, the derivative of neuraminic acid is Neu5Gc and the derivative of mannosamine is N-glycolylmannosamine.

According to certain embodiments, the derivative of neuraminic acid is 2-keto-3-deoxy-D-glycero-D-galacto-nononic acid and the derivative of mannosamine is D-mannose.

According to certain embodiments, incubation is carried out at a temperature ranging from about 0 to about 30° C., such as from about 4 to about 25° C. According to particular embodiments, incubation is carried out at a temperature ranging from about 10 to about 25° C. According to more particular embodiments, incubation is carried out at a temperature ranging from about 15 to about 25° C. According to other more particular embodiments, incubation is carried out at a temperature ranging from about 18 to about 25° C. According to other more particular embodiments, incubation is carried out at a temperature ranging from about 19 to about 25° C. According to other more particular embodiments, incubation is carried out at a temperature ranging from about 20 to about 25° C. According to other more particular embodiments, incubation is carried out at a temperature ranging from about 15 to about 23° C. According to other more particular embodiments, incubation is carried out at a temperature ranging from about 17 to about 23° C. According to other more particular embodiments, incubation is carried out at a temperature ranging from about 18 to about 23° C. According to other more particular embodiments, incubation is carried out at a temperature ranging from about 19 to about 23° C. According to other more particular embodiments, incubation is carried out at a temperature ranging from about 20 to about 23° C. According to other more particular embodiments, incubation is carried out at a temperature ranging from about 15 to about 22° C. According to other more particular embodiments, incubation is carried out at a temperature ranging from about 17 to about 22° C. According to other more particular embodiments, incubation is carried out at a temperature ranging from about 18 to about 22° C. According to other more particular embodiments, incubation is carried out at a temperature ranging from about 19 to about 22° C. According to other more particular embodiments, incubation is carried out at a temperature ranging from about 20 to about 22° C. According to other more particular embodiments, incubation is carried out at a temperature ranging from about 15 to about 21° C. According to other more particular embodiments, incubation is carried out at a temperature ranging from about 17 to about 21° C. According to other more particular embodiments, incubation is carried out at a temperature ranging from about 18 to about 21° C. According to other more particular embodiments, incubation is carried out at a temperature ranging from about 19 to about 21° C.

For example, the incubation may be carried out at about 20° C.

According to certain other embodiments, incubation is carried out at a temperature ranging from about 30 to about 80° C., such as from about 50 to about 70° C. According to particular embodiments, incubation is carried out at a temperature ranging from about 60 to about 70° C., such as from about 62 to about 68° C. According to more particular embodiments, incubation is carried out at a temperature ranging from about 63 to about 67° C., such as from about 64 to about 66° C. For example, incubation may be carried out at about 65° C.

The incubation may take as long as it takes for completely cleaving neuraminic acid.

However, according to certain embodiments, incubation is carried out for a time period of at least about 6 hours. According to certain other embodiments, incubation is carried out for a time period of at least about 12 hours. According to certain other embodiments, incubation is carried out for a time period of at least about 48 hours. According to certain other embodiments, incubation is carried out for a time period of at least about 36 hours.

According to certain other embodiments, incubation is carried out for a time period of at least about 24 hours. According to certain other embodiments, incubation is carried out for a time period of at least about 36 hours. According to certain other embodiments, incubation is carried out for a time period of at least about 48 hours. According to certain other embodiments, incubation is carried out for a time period of at least about 60 hours.

According to certain other embodiments, incubation is carried out for a time period of at least about 72 hours.

For example, incubation may be carried out for a time period of at the most 96 hours. According to certain other embodiments, incubation is carried out for a time period of at the most about 72 hours. According to certain other embodiments, incubation is carried out for a time period of at the most about 60 hours. According to certain other embodiments, incubation is carried out for a time period of at the most about 48 hours. According to certain other embodiments, incubation is carried out for a time period of at the most about 24 hours. According to certain other embodiments, incubation is carried out for a time period of at the most about 12 hours.

According to certain embodiments, incubation is carried out at a pH ranging from about 7 to about 9, such as from about 7.5 to about 8.5. According to particular embodiments, incubation is carried out at a pH ranging from about 8 to about 9, such as from about 8 to about 8.5.

In order to obtain the desired pH, any suitable buffering agent suitable for maintaining such pH known in the art may be used. Suitable buffering agents for use according to this aspect include, but are not limited to, Tris (2-Amino-2-(hydroxymethyl)-propan-1,3-diol), HEPES (4-(2-hydroxyethyl)-1-piperazineethanesulfonic acid), triethanolamine, MOPS, MOBS and DIPSO. The skilled person is aware of appropriate amounts of the respective buffering agent to be employed.

According to certain embodiments, the method further comprises b') determining the amount of mannosamine or derivative thereof, such as N-acetylmannosamine, or the amount of pyruvate.

According to certain embodiments, the method further comprises b') determining the amount of mannosamine or derivative thereof, such as N-acetylmannosamine.

The amount of mannosamine or derivative thereof, such as N-acetylmannosamine, can be determined by any suitable technique known in the art, such as by use of a fluorescent dye or by radiolabeling. Therefore, according to particular embodiments, the amount of N-acetylmannosamine is determined by use of a fluorescent dye. According to other particular embodiments, the amount of N-acetylmannosamine is determined by radiolabeling.

According to certain other embodiments, the method further comprises b') determining the amount of pyruvate.

The amount of pyruvate can be determined by any suitable technique known in the art, such as by quantitating NADH oxidation. This technique involves the use of an enzyme, such as lactic dehydrogenase, which catalyzes a reaction by which pyruvate is reduced and NADH is oxidized. The NADH oxidation may then be quantitated, e.g., spectrophotometrically.

Accordingly, a method for quantitating neuraminic acid or derivative thereof according to the present invention may involve a coupled enzyme reaction, converting neuraminic acid or a said derivative, such as N-acetylneuraminic acid (Neu5Ac), into mannosamine and pyruvate in the presence of a polypeptide comprising the amino acid sequence as set forth in SEQ ID NO: 1 or a functional variant thereof, and reducing pyruvate in the presence of NADH using an enzyme, lactic dehydrogenase. NADH oxidation may then be quantitated by any suitable technique known in the art, such as spectrophotometrically.

Alternatively, the amount of pyruvate can be determined by quantitating hydrogen peroxide. This technique involves the use of an enzyme, such as pyruvate oxidase, which catalyzes a reaction where pyruvate is converted into acetylphosphate and hydrogen peroxide. Hydrogen peroxide may then be quantitated by any suitable technique known in the art, such colorimetrically, fluorometrically or spectrophotometrically using, e.g., an horseradish peroxidase (HRP) based assay.

Accordingly, a method for quantitating neuraminic acid or derivative thereof according to the present invention may involve a coupled enzyme reaction, converting neuraminic acid or a said derivative, such as such as N-acetylneuraminic acid (Neu5Ac), into mannosamine and pyruvate in the presence of a polypeptide comprising the amino acid sequence as set forth in SEQ ID NO: 1 or a functional variant thereof, and converting pyruvate into e.g. acetylphosphate and hydrogen peroxide using an enzyme, such as pyruvate oxidase. Hydrogen peroxide may then be quantitated colorimetrically, fluorometrically or spectrophotometrically using, e.g., an horseradish peroxidase (HRP) based assay.

From the results of the quantification of the amount of mannosamine (or derivative) or pyruvate in the sample, the skilled person can easily determine the amount of neuraminic acid or derivative thereof in the sample.

The quantification may include the comparison of obtained values to a standard curve. The preparation and use of a standard curve in quantification is well known to the skilled person.

Since the sample of interest may contain free mannosamine or pyruvate as a contaminant, a sample blank may be prepared. The sample blank should be processed under the same conditions as the sample of interest, but in the absence of a polypeptide according to the invention. The preparation and use of a sample blank in quantification is well known to the skilled person.

The present invention also provides a method for quantitating neuraminic acid or derivative thereof, such as N-acetylneuraminic acid (Neu5Ac), in a sample, such as a biological sample, the method comprising:

a') incubating said sample in the presence of a N-acetylneuraminate lyase from a bacterium of the Vibrionaceae family or a functional variant thereof.

According to certain embodiments, the method further comprises b') determining the amount of mannosamine or derivative thereof, such as N-acetylmannosamine.

The amount of mannosamine or derivative thereof, such as N-acetylmannosamine, can be determined by any suitable technique known in the art, such as by use of a fluorescent dye or by radiolabeling. Therefore, according to particular embodiments, the amount of N-acetylmannosamine is determined by use of a fluorescent dye. According to other particular embodiments, the amount of N-acetylmannosamine is determined by radiolabeling.

According to certain other embodiments, the method further comprises b') determining the amount of pyruvate.

The amount of pyruvate can be determined by any suitable technique known in the art, such as by quantitating NADH oxidation. This technique involves the use of an enzyme, such as lactic dehydrogenase, which catalyzes a reaction by which pyruvate is reduced and NADH is oxidized. The NADH oxidation may then be quantitated, e.g., spectrophotometrically.

Accordingly, a method for quantitating neuraminic acid or derivative thereof according to the present invention may involve a coupled enzyme reaction, converting neuraminic acid or a said derivative, such as such as N-acetylneuraminic acid (Neu5Ac), into mannosamine and pyruvate in the presence of a polypeptide comprising the amino acid sequence as set forth in SEQ ID NO: 1 or a functional variant thereof, and reducing pyruvate in the presence of NADH using an enzyme, lactic dehydrogenase. NADH oxidation may then be quantitated by any suitable technique known in the art, such as spectrophotometrically.

Alternatively, the amount of pyruvate can be determined by quantitating hydrogen peroxide. This technique involves the use of an enzyme, such as pyruvate oxidase, which catalyzes a reaction by which pyruvate is converted into acetylphosphate and hydrogen peroxide. Hydrogen peroxide may then be quantitated by any suitable technique known in the art, such colorimetrically, fluorometrically or spectrophotometrically using, e.g., an horseradish peroxidase (HRP) based assay.

Accordingly, a method for quantitating neuraminic acid or derivative thereof according to the present invention may involve a coupled enzyme reaction, converting neuraminic acid or a said derivative, such as such as N-acetylneuraminic acid (Neu5Ac), into mannosamine and pyruvate in the presence of a polypeptide comprising the amino acid sequence as set forth in SEQ ID NO: 1 or a functional variant thereof, and converting pyruvate into e.g. acetylphosphate and hydrogen peroxide using an enzyme, such as pyruvate oxidase.

Hydrogen peroxide may then be quantitated colorimetrically, fluorometrically or spectrophotometrically using, e.g., an horseradish peroxidase (HRP) based assay.

From the results of the quantification of the amount of mannosamine (or derivative) or pyruvate in the sample, the skilled person can easily determine the amount of neuraminic acid or derivative thereof in the sample.

The quantification may include the comparison of obtained values to a standard curve. The preparation and use of a standard curve in quantification is well known to the skilled person.

Since the sample of interest may contain free mannosamine or pyruvate as a contaminant, a sample blank may be prepared. The sample blank should be processed under the same conditions as the sample of interest, but in the absence of a polypeptide according to the invention. The preparation and use of a sample blank in quantification is well known to the skilled person.

It is understood that details given in the context of the foregoing aspect, in particular with respect to certain condition such as pH, temperature, timing etc., apply mutatis mutandis to this aspect of the invention.

According to certain embodiments, the N-acetylneuraminate lyase is from a bacterium of the genus *Aliivibrio*.

According to particular embodiments, the N-acetylneuraminate lyase is from a bacterium selected from *Aliivibrio salmonicida*, *Aliivibrio logei*, *Aliivibrio wodanis*, *Aliivibrio fischeri*, *Aliivibrio finisterrensis* or *Aliivibrio siliae*.

According to more particular embodiments, the N-acetylneuraminate lyase is from the bacterium *Aliivibrio salmonicida*.

According to certain embodiments, the bacterium is a psychrophilic bacterium.

The present invention provides a kit comprising i) a polypeptide comprising the amino acid sequence as set forth in SEQ ID NO: 1 or a functional variant thereof.

According to certain embodiments, a kit may further comprise an enzyme, such as pyruvate oxidase, which catalyzes a reaction by which pyruvate is converted into acetylphosphate and hydrogen peroxide.

According to particular embodiments, a kit may further comprise means for quantitating hydrogen peroxide, such as horseradish peroxidase (HRP) and/or suitable substrate (e.g., TMB substrate).

According to certain embodiments, a kit may further comprise an enzyme, such as lactic dehydrogenase, which catalyzes a reaction by which pyruvate is reduced and NADH is oxidized.

According to particular embodiments, a kit may further comprise NADH.

Kits according to the present invention may further comprise suitable reaction buffers.

GENERAL DEFINITIONS

A variant, such as a functional variant, within the meaning of the present invention is a polypeptide comprising an amino acid sequence having at least about 80%, such as at least about 85%, at least about 90%, at least about 95%, at least about 96%, at least about 97%, at least about 98%, or at least about 99%, sequence identity to the amino acid sequence of a reference polypeptide and preferably has the same or similar catalytic activity as the reference polypeptide. In accordance to certain aspects of the present invention, a variant, and more particular a functional variant, is a polypeptide comprising an amino acid sequence having at least about 80%, such as at least about 85%, at least about 90%, at least about 95%, at least about 96%, at least about 97%, at least about 98%, or at least about 99%, sequence identity to the amino acid sequence set forth in SEQ ID NO: 1.

According to particular embodiments, the functional variant preferably has at least one of the following properties i) to iii):

i) a pH optimum for the condensation reaction of about 7.5 to about 8;
ii) the activity ($\mu$mol min$^{-1}$) of the condensation reaction is retained at a level of at least 80%, such as at least about 83%, at least about 85% or at least about 90%, of the initial activity following storage for 30 days at 23° C. in glycine buffer at pH 11;
iii) a specific activity of the condensation reaction in the range from about 0.0435 to about 0.0725 $\mu$mol min$^{-1}$ mg$^{-1}$, such as in the range from about 0.0522 to about 0.0638 $\mu$mol min$^{-1}$ mg$^{-1}$, such as about 0.058 $\mu$mol min$^{-1}$ mg$^{-1}$.

The specific activity of the condensation reaction may be (e.g., is) measured after 30 minutes incubation at 23° C. employing 7 $\mu$g polypeptide, 20 mM N-acetylmannosamine, 80 mM pyruvate and 124 mM HEPES, pH 8.0, in a total of 250 $\mu$l reaction mixture.

The activity or specific activity of a polypeptide of the invention may, for instance, be assessed using the modified thiobarbituric acid (TBA) assay developed by Aminoff (1961) and Warren (1959), which is described in Example 2 "Enzyme activity assay", below.

According to more particular embodiments, a variant, such as a functional variant, is a polypeptide comprising an amino acid sequence having at least about 80%, such as at least about 85%, at least about 90%, at least about 95%, at least about 96%, at least about 97%, at least about 98%, or at least about 99%, sequence identity to the amino acid sequence set forth in SEQ ID NO: 1, and having at least property i), and preferably property ii).

According to other more particular embodiments, a variant, such as a functional variant, is a polypeptide comprising an amino acid sequence having at least about 80%, such as at least about 85%, at least about 90%, at least about 95%, at least about 96%, at least about 97%, at least about 98%, or at least about 99%, sequence identity to the amino acid sequence set forth in SEQ ID NO: 1, and having at least property i), and preferably property iii).

According to other more particular embodiments, a variant, such as a functional variant, is a polypeptide comprising an amino acid sequence having at least about 80%, such as at least about 85%, at least about 90%, at least about 95%, at least about 96%, at least about 97%, at least about 98%, or at least about 99%, sequence identity to the amino acid sequence set forth in SEQ ID NO: 1, and having at least property ii), and preferably property iii).

According to other more particular embodiments, a variant, such as a functional variant, is a polypeptide comprising an amino acid sequence having at least about 80%, such as at least about 85%, at least about 90%, at least about 95%, at least about 96%, at least about 97%, at least about 98%, or at least about 99%, sequence identity to the amino acid sequence set forth in SEQ ID NO: 1, and having at least property iii), and preferably property ii).

According to other more particular embodiments, a variant, such as a functional variant, is a polypeptide comprising an amino acid sequence having at least about 80%, such as at least about 85%, at least about 90%, at least about 95%, at least about 96%, at least about 97%, at least about 98%, or at least about 99%, sequence identity to the amino acid sequence set forth in SEQ ID NO: 1, and having at least properties ii) and iii), and preferably property i).

According to other more particular embodiments, a variant, such as a functional variant, is a polypeptide comprising an amino acid sequence having at least about 90% sequence identity to the amino acid sequence set forth in SEQ ID NO: 1.

Within the context of the present invention, term "% identity" of an amino acid sequence to a reference amino acid sequence, as used herein, defines the % identity calculated from the two amino acid sequences as follows: The sequences are aligned using Version 9 of the Genetic Computing Group's GAP (global alignment program), using the default BLOSUM62 matrix (see below) with a gap open penalty of −12 (for the first null of a gap) and a gap extension penalty of −4 (for each additional null in the gap). After alignment, percentage identity is calculated by expressing the number of matches as a percentage of the number of amino acids in the reference amino acid sequence.

The following BLOSUM62 matrix is used:

| | | | | | | | | | | | | | | | | | |
|---|---|---|---|---|---|---|---|---|---|---|---|---|---|---|---|---|---|
| Ala | 4 | | | | | | | | | | | | | | | | |
| Arg | −1 | 8 | | | | | | | | | | | | | | | |
| Asn | −2 | 0 | 6 | | | | | | | | | | | | | | |
| Asp | −2 | −2 | 1 | 6 | | | | | | | | | | | | | |
| Cys | 0 | −3 | −3 | −3 | 9 | | | | | | | | | | | | |
| Gln | −1 | 1 | 0 | 0 | −3 | 6 | | | | | | | | | | | |
| Glu | −1 | 0 | 0 | 2 | −4 | 2 | 5 | | | | | | | | | | |
| Gly | 0 | −2 | 0 | −1 | −3 | −2 | −2 | 6 | | | | | | | | | |
| His | −2 | 0 | 1 | −1 | −3 | 0 | 0 | −2 | 6 | | | | | | | | |
| Ile | −1 | −3 | −3 | −3 | −1 | −3 | 3 | −4 | −3 | 4 | | | | | | | |
| Leu | −1 | −2 | −3 | −4 | −1 | −2 | −3 | −4 | −3 | 2 | 4 | | | | | | |
| Lys | −1 | 2 | 0 | −1 | −3 | 1 | 1 | −2 | −1 | −3 | −2 | 6 | | | | | |
| Met | −1 | −1 | −2 | −3 | −1 | 0 | −2 | −3 | −2 | 1 | 2 | −1 | 6 | | | | |
| Phe | −2 | −3 | −3 | −3 | −2 | −3 | −3 | −3 | −1 | 0 | 0 | −3 | 6 | 6 | | | |
| Pro | −1 | −2 | −2 | −1 | −3 | −1 | −1 | −2 | −2 | −3 | −3 | −1 | −2 | −4 | 7 | | |
| Ser | 1 | −1 | 1 | 0 | −1 | 0 | 0 | 0 | −1 | −2 | −2 | 0 | −1 | −2 | −1 | 4 | |
| Thr | 0 | −1 | 0 | −1 | −1 | −1 | −1 | −2 | −2 | −1 | −1 | −1 | −1 | −2 | −1 | 1 | 8 |

-continued

| Trp | -3 | -3 | -4 | -4 | -2 | -2 | -3 | -2 | -2 | -3 | -2 | -3 | -1 | 1 | -4 | -3 | -2 | 11 | |
|---|---|---|---|---|---|---|---|---|---|---|---|---|---|---|---|---|---|---|---|
| Tyr | -2 | -2 | -2 | -3 | -2 | -1 | -2 | -3 | 2 | -1 | -1 | -2 | -1 | 3 | -3 | -2 | -2 | 2 | 7 |
| Val | 0 | -3 | -3 | -3 | -1 | -2 | -2 | -3 | -3 | 3 | 1 | -2 | 1 | -1 | -2 | -2 | 0 | -3 | -1 | 4 |
| | Ala | Arg | Asn | Asp | Cys | Gln | Glu | Gly | His | Ile | Leu | Lys | Met | Phe | Pro | Ser | Thr | Trp | Tyr | Val |

A derivative of neuraminic acid within the meaning of the present invention may be any derivative of neuraminic acid known in the art. The derivative of neuraminic acid may be an N- or O-substituted neuraminic acid, such as an N-acetylated or N-glycolylated neuraminic acid. Non-limiting examples of such derivatives include N-acetylneuraminic acid (Neu5Ac) or N-glycolylneuraminic acid (Neu5Gc), and respective O-substituted derivatives thereof, such as O-acetyl derivatives thereof. According to certain embodiments, the derivative of neuraminic acid is N-acetylneuraminic acid (Neu5Ac) or an O-substituted derivative thereof, such as an O-acetyl derivative thereof, such as 7-O-acetyl-N-acetylneuraminic acid (Neu5, 7Ac2) or 9-O-acetyl-N-acetylneuraminic acid (Neu5, 9 Ac2). According to other certain embodiments, the derivative of neuraminic acid is N-glycolylneuraminic acid (Neu5Gc) or an O-substituted derivative thereof, such as an O-acetyl derivative thereof, such as 7-O-acetyl-N-glycolylneuraminic acid (Neu5, 7Gc2) or 9-O-acetyl-N-acetylmannosamine. According to particular embodiments, the derivative of neuraminic acid is N-acetylneuraminic acid (Neu5Ac). According to other particular embodiments, the derivative of neuraminic acid is an O-substituted derivative of N-acetylneuraminic acid (Neu5Ac), such as an O-acetyl derivative of N-acetylneuraminic acid (Neu5Ac). Such O-acetyl derivative may, for instance, be 7-O-acetyl-N-acetylneuraminic acid (Neu5, 7Ac2). According to other particular embodiments, the derivative of neuraminic acid is N-glycolylneuraminic acid (Neu5Gc). According to other particular embodiments, the derivative of neuraminic acid is an O-substituted derivative of N-glycolylneuraminic acid (Neu5Gc), such as an O-acetyl derivative of N-glycolylneuraminic acid (Neu5Gc). Such O-acetyl derivative may, for instance, be 7-O-acetyl-N-glycolylneuraminic acid (Neu5, 7Gc2).

A derivative of glucosamine within the meaning of the present invention (and employed in accordance with the present invention) may be any derivative of glucosamine known in the art. The derivative of glucosamine may be an N- or O-substituted glucosamine, such as an N-acetylated or N-glycolylated glucosamine. Non-limiting examples of such derivatives include N-acetylglucosamine (GlcNAc) or N-glycolylglucosamine (GlcNGc), and respective O-substituted derivatives thereof, such as O-acetyl derivatives thereof. According to certain embodiments, the derivative of glucosamine is N-acetylglucosamine (GlcNAc) or an O-substituted derivative thereof, such as an O-acetyl derivative thereof, such as 4-O-acetyl-N-acetylglucosamine, 6-O-acetyl-N-acetylglucosamine or 9-O-acetyl-N-acetylglucosamine. According to other certain embodiments, the derivative of glucosamine is N-glycolylglucosamine (GlcNGc) or an O-substituted derivative thereof, such as an O-acetyl derivative thereof, such as 4-O-acetyl-N-glycolylglucosamine, 6-O-acetyl-N-glycolylglucosamine, 9-O-acetyl-N-glycolylglucosamine. According to particular embodiments, the derivative of glucosamine is N-acetylglucosamine (GlcNAc). According to other particular embodiments, the derivative of glucosamine is an O-substituted derivative of N-acetylglucosamine (GlcNAc), such as an O-acetyl derivative of N-acetylglucosamine (GlcNAc). Such O-acetyl derivative may, for instance, be 4-O-acetyl-N-acetyl glucosamine. According to other particular embodiments, the derivative of glucosamine is N-glycolylglucosamine (GlcNGc). According to other particular embodiments, the derivative of glucosamine is an O-substituted derivative of N-glycolylglucosamine (GlcNGc), such as an O-acetyl derivative of N-glycolylglucosamine (GlNGc). Such O-acetyl derivative may, for instance, be 4-O-acetyl-N-glycolylglucosamine.

A derivative of mannosamine within the meaning of the present invention (and employed in accordance with the present invention) may be any derivative of mannosamine known in the art. The derivative of mannosamine may be an N- or O-substituted mannosamine, such as an N-acetylated or N-glycolylated mannosamine. Non-limiting examples of such derivatives include N-acetylmannosamine (ManNAc), N-glycolylmannosamine (ManNGc), and respective O-substituted derivatives thereof, such as O-acetyl derivatives thereof. According to certain embodiments, the derivative of mannosamine is N-acetylmannosamine (ManNAc) or an O-substituted derivative thereof, such as an O-acetylated derivative thereof, such as 4-O-acetyl-N-acetylmannosamine, 6-O-acetyl-N-acetylmannosamine or 9-O-acetyl-N-acetylmannosamine.

According to other certain embodiments, the derivative of mannosamine is N-glycolylmannosamine (ManNGc) or an O-substituted derivative thereof, such as an O-acetyl derivative thereof, such as 4-O-acetyl-N-glycolylmannosamine, 6-O-acetyl-N-glycolylmannosamine or 9-O-acetyl-N-glycolylmannosamine.

According to particular embodiments, the derivative of mannosamine is N-acetylmannosamine (ManNAc). According to other particular embodiments, the derivative of glucosamine is an O-substituted derivative of N-acetylmannosamine (ManNAc), such as an O-acetyl derivative of N-acetylmannosamine (ManNAc). Such O-acetyl derivative may, for instance, be 4-O-acetyl-N-acetylmannosamine. According to other particular embodiments, the derivative of glucosamine is N-glycolylmannosamine (ManNGc). According to other particular embodiments, the derivative of glucosamine is an O-substituted derivative of N-glycolylmannosamine (ManNGc), such as an O-acetyl derivative of N-glycolylmannosamine (ManNGc). Such O-acetyl derivative may, for instance, be 4-O-acetyl-N-glycolylmannosamine.

Where a numerical limit or range is stated herein, the endpoints are included. Also, all values and sub ranges within a numerical limit or range are specifically included as if explicitly written out.

Having generally described this invention, a further understanding can be obtained by reference to certain specific examples, which are provided herein for purposes of illustration only, and are not intended to be limiting unless otherwise specified.

EXAMPLES

Example 1

Production of AsNAL

Bacterial Strains and Plasmids

*A. salmonicida* LFI1238 originally isolated from diseased cod (*Gadhus morhua*), was kindly provided by Elin Sandaker (Norwegian Institute of Fisheries and Aquaculture Research, Tromsø, Norway). Genomic DNA was extracted using the Wizard Genomic DNA Purification Kit (Promega), following the manufacturers' instructions. Chemically competent Top 10 cells, pDONR221, pDEST14 and pDEST17 were from Invitrogen. *E. coli* One Shot BL21 Star DE3 strain was from Invitrogen.

Cloning and Expression

Two constructs of the gene encoding AsNAL were designed and amplified using polymerase chain reaction (PCR). The first construct contains a hexahistidine tag and a Tobacco Etch Virus cleavage site in the N-terminus, whereas the second construct contains a hexahistidine tag at the C-terminus. The PCR primers (Sigma) are shown in Table 1.

TABLE 1

PCR primers used in the cloning of AsNAL. FPN1 and FPN2 are the forward primers for the N-terminal construct and FPC1 and FPC2 are for the C-terminal construct. RPN1 and RPN2 are the reverse primers for the N-terminal construct and RPC1 and RPC2 for the C-terminal construct.

| Primer Name | Primer sequence |
| --- | --- |
| FPN1 | 5'-TTCGAAAACCTGTATTTTCAGGGCA TGAAAAGTTAACAGGTTTAATTG-3' |
| FPN2 | 5'-GGGGACAAGTTTGTACAAAAAAGCA GGCTTCGAAAACCTG-3' |
| FPC1 | 5'-GGAGATAGAACCATGAAAAAGTTAA CAGGTTTAATTG-3' |
| FPC2 | 5'-GGGGACAAGTTTGTACAAAAAAGCA GGCTTCGAAGGAGATAGAACC-3' |
| RPN1 | 5'-GAAAGCTGGGTGTTATTTAAGAAAA TTTGCGGCTCTC-3' |
| RPN2 | 5'-GGGGACCACTTTGTACAAGAAAGCT GGGTGTTA-3' |
| RPC1 | 5'-TTAGTGGTGGTGGTGGTGTTTA AGAAAATTTGCGGCTCTC-3' |
| RPC2 | 5'-GGGACCACTTTGTACAAGAAAGCTG GGTCTTAGTGGTGGTGGTGGTG-3' |

The gene encoding AsNAL, denoted nanA, was initially amplified using the forward primers FPN1 and FPC1 and the reverse primers RPN1 and RPC1, for N-terminally and C-terminally tagged constructs, respectively. The total volume of the PCR reaction was 50 µl containing 1U Phusion High-Fidelity DNA Polymerase (Finnzymes), 1× buffer supplied by the manufacturer, 0.3 mM dNTPs, 0.3 µM of each of the forward and reverse primers and template DNA (genomic DNA of *A. salmonicida*). The PCR was carried out at 98° C. for 2 min, followed by 35 cycles of denaturation (98° C. for 20 s), annealing (50° C. for 20 s), extension (72° C. for 20 s) and final extension at 72° C. for 7 min. The resultant PCR products were purified from a 1% agarose gel using the Qiaquick Gel Extraction Kit (Qiagen) and subsequently used as templates in a second PCR with the forward primers FPN2 and FPC2 and the reverse primers RPN2 and RPC2 for the N-terminally and C-terminally tagged constructs, respectively. The PCR2 products were purified in the same way as the first PCR product. The final attB-PCR products were inserted into the destination vector pDEST17 (N-terminal His-tag construct) and pDEST14 (C-terminal His-tag construct) using BP- and LR-clonase reactions following the "One-Tube Protocol" (Gateway Technology, Invitrogen). The destination vectors containing the nanA constructs were used to transform chemically competent *E. coli* TOP 10 cells. The expression plasmids were purified using Plasmid DNA Purification Kit (Qiagen) and sequenced to confirm their identity. *E. coli* One Shot BL21 Star DE3 cells were used for large scale expression. A 10 ml overnight preculture (LB-medium containing 100 µg/ml ampicillin) was used to inoculate 1 L of sterile growth-medium. Cells were grown in an orbital shaker at 180 rpm and 37° C. until OD600 reached 0.6. Protein expression was then induced by adding 0.5 mM isopropyl β-D-1-thiogalactopyranoside (IPTG) after reducing temperature to 20° C. The cells were grown further overnight. The cells were harvested by centrifugation at 8950×g (JLA 8.1000 rotor) for 25 min at 4° C.

Purification

Bacterial cell pellets were resuspended in lysis buffer (50 mM Tris-HCl pH 7.5, 500 mM NaCl, 5 mM 2-Mercaptoethanol (β-ME), 10% Glycerol) containing an ethylenediaminetetraacetic acid (EDTA)-free proteinase inhibitor cocktail tablet (Roche) and DNAseI (Invitrogen). The cells were disrupted by sonication (Vibra-cell, Sonics & Materials, Inc.) on ice using pulse on/off 9.9 s, temperature set to 20° C., amplitude to 25% and total sonication time 30 min. The sonicated extract was centrifuged to remove cell debris (9000×g, 30 min, 4° C.). Purification was carried out at room temperature using Akta Explorer purification system (GE Healthcare). Filtered (0.45 µm) crude protein extract (about 40 ml) was loaded onto a HisTrap affinity column equilibrated with buffer A1 (50 mM Tris-HCl pH 7.5, 500 mM NaCl, 10 mM Imidazole, 5 mM β-ME and 10% Glycerol). Loosely bound impurities were washed out with 5% buffer B1 (50 mM Tris-HCl pH 7.5, 500 mM NaCl, 500 mM Imidazole, 5 mM β-ME and 10% Glycerol). Bound protein was eluted using a gradient of 5-100% buffer B1. For the construct with a TEV-cleavable N-terminal His-tag, fractions containing the enzyme were pooled and dialyzed overnight in TEV-cleavage buffer (50 mM Tris-HCl pH 7.5, 500 mM NaCl, 1 mM β-ME and 1 mM EDTA) using Pierce Slide-A-Lyzer dialysis cassettes with a 3.5 kDa molecular weight cutoff, (Thermo Fisher Scientific Inc.) and further digested overnight with TEV protease (1 mg of TEV protease per 5 mg of AsNAL) to remove the His6-tag from the protein. After digestion, the mixture was dialyzed again overnight in buffer A1 and loaded onto a HisTrap affinity column equilibrated with buffer A1. The digested protein was collected in the flow-through. Fractions containing the enzyme were pooled and concentrated to 5 ml by using a 10 kDa cutoff Amicon Ultra spin-column (Millipore). The sample was loaded onto a Superdex 200 prep grade Hiload (16/60) Gel filtration column equilibrated in buffer A2 (50 mM Tris-HCl pH 7.5, 500 mM NaCl, 5 mM β-ME and 10% Glycerol). The construct with C-terminal His-tag was purified using only one HisTrap step. Purity of the protein was assessed by (SDS-PAGE) using Tris-HCl Mini-PROTEAN® TGX™ Precast gels (Bio-Rad Laboratories) and bands of interest were excised from the gel and sent for mass spectrometry (MS) analysis (Q-TOF UltimaGlobal MS, Micromass) to confirm purification of the correct protein. Native molecular weight of the protein was determined by the gel filtration chromatography and native PAGE. Protein concentrations were determined by using both a nanodrop spectrophotometer and the Bio-Rad Protein Assay (Bio-Rad Laboratories) according to the microtiter plate protocol described by the manufacturer using bovine serum albumin (BSA) as a standard.

Results

E. coli One Shot BL21 Star DE3 cells were transformed with the expression plasmid pDEST17 containing the gene encoding AsNAL downstream a His6-tag coding sequence and a TEV protease site. The protein was soluble when expressed at 20° C. and purified in three consecutive steps using Ni2+ (HisTrap) affinity and Superdex 200 (16/60) gel filtration chromatography. The protein band at 32 kDa shown in FIG. 1A demonstrates the purity of the protein after gel filtration and the expected molecular weight of the monomer subunit. Native PAGE of AsNAL (FIG. 1B) shows a single band close to 123 kDa. Being approximately four times the weight of the monomer, this indicates that the soluble entity is a tetramer.

By the above it has been shown that AsNAL could be expressed and purified to homogeneity. From native PAGE, it was evident that AsNAL is tetrameric in solution. This is in accordance with what is reported for NALs purified from other organisms, although there are reports of EcNAL being a trimer and CpNAL a dimer.

Example 2

Characterisation of AsNAL

Enzyme Activity Assay

Both the condensation and cleavage activities of NAL were assessed using the modified thiobarbituric acid (TBA) assay developed by Aminoff (1961) and Warren (1959). The condensation activity was determined by incubating 50 µl of a reaction mixture containing 15 mM sodium pyruvate, 15 mM ManNAc, 124 mM HEPES pH 8.0 and different concentrations of enzyme depending on assay type at selected temperatures for the required amount of time. The reaction was terminated by adding 137 µl 2.5 mg/ml sodium periodate in 57 mM $H_2SO_4$, followed by incubation at 37° C. for 15 min with shaking at 1350 rpm. Sodium arsenite (50 µl, 25 mg/ml sodium arsenite in 0.5 M HCl) was added resulting in brown color. The tubes were shaken manually until the brown color disappeared. 2-thiobarbituric acid solution (100 µl, 71 mg/ml adjusted to pH 9.0) was subsequently added, and the tubes were incubated in boiling water for 7.5 min. The tubes were incubated on ice for 5 min and allowed to remain at room temperature for 5 min. The red chromophore was extracted by addition of acidic butanol (1 ml of acidic butanol with 5% HCl) and horizontal shaking for 10 min. Tubes were centrifuged at 16060×g, 7 min (room temperature) to separate the organic and inorganic phases. The organic phase containing the red chromophore (200 µl) was used for measurement of absorbance at 549 nm in a spectrophotometer (SpectraMax M2e, Molecular Devices). The amount of Neu5Ac produced was inferred from a standard curve. To generate a standard curve, different concentrations of Neu5Ac (0.031 mM-1 mM) were treated with 137 µl of 2.5 mg/ml sodium periodate in 57 mM $H_2SO_4$ and the TBA assay procedure was followed as described above.

The cleavage activity was determined by incubating 50 µl of a reaction mixture containing 5 mM Neu5Ac, 124 mM HEPES pH 8.0 and different concentrations of enzyme depending on assay type at selected temperatures for the required amount of time. Termination of the reactions and subsequent steps of the assay are as described above. The decrease in absorbance is correlated to the increase in cleavage activity.

Activity at Different pH and Temperatures pH profiles were determined by assaying the enzyme in triplicate for both condensation and cleavage directions at pH values ranging from 5.5 to 11.0 with 0.5 pH unit intervals. Sodium phosphate buffer was used from pH 5.5 to 7.5, HEPES buffer from pH 6.5 to 8.0, Tris-HCl buffer from pH 7.5 to 9.0 and Glycine buffer from pH 9.0 to 11.0. The reaction mixture was incubated at room temperature for 1 h before being subjected to the TBA assay. Temperature profiles were determined for both directions by assaying the enzyme in triplicate from 4 to 80° C. in HEPES buffer pH 8.0. The reaction mixture was incubated for 30 min at selected temperatures and the reaction was terminated by adding 2 µl of concentrated $H_2SO_4$ and then subjected to the TBA assay.

Results: pH and Temperature Profiles

Figure 2:
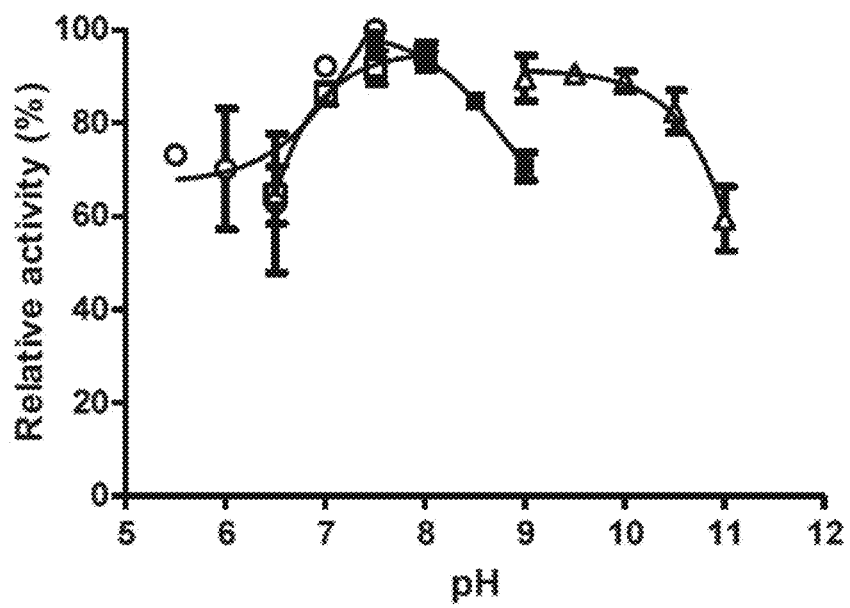
FIG. 2. pH- and temperature profiles for AsNAL determined by the TBA assay. (A) pH profile for the condensation reaction. (B) pH profile for the cleavage reaction. The buffers used were Sodium phosphate pH 5.5-7.5 (open circles), HEPES pH 6.5-8.0 (open squares), Tris-HCl pH 7.5-9.0 (black squares), and Glycine pH 9.0-11.0 (open triangles). (C) Temperature profile of AsNAL in HEPES buffer pH 8.0 for the condensation (open circles), and cleavage (black circles) reactions. Activity is relative to the highest value measured.
Figure 2:
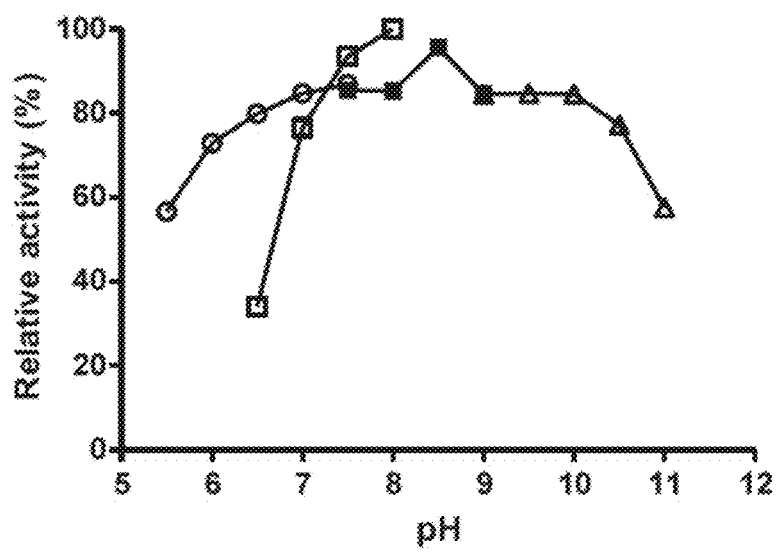
Figure 2:
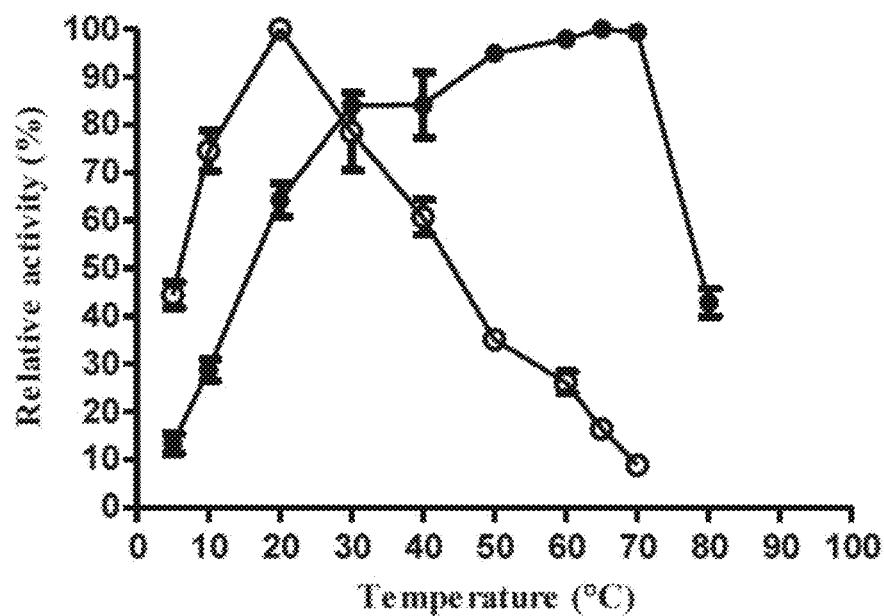

The effect of pH on the enzyme activity was studied for both the condensation and the cleavage reactions (FIGS. 2A and 2B). The enzyme was active over a wide pH range in both reactions. Maximum activity was obtained between pH 7.5 (sodium phosphate and Tris-HCl buffers) and 8.0 (HEPES buffer) for the condensation reaction, whereas maximum activity was obtained between pH 8.0 (HEPES buffer) and pH 8.5 (Tris-HCl buffer) for the cleavage reaction. The temperature profiles for both the condensation and the cleavage reactions are shown in FIG. 2C. The optimal temperature was 20° C. for the condensation reaction, whereas it was at 65° C. for the cleavage reaction. The temperature profile for the cleavage reaction is broader than what is observed for the condensation reaction. The enzyme retained 75% of its condensation activity and 30% of its cleavage activity at 10° C.

Condensation-Cleavage Equilibrium Studies

In order to determine the equilibrium constant between reactants and products, activity at different temperatures was determined by incubating 50 µl of reaction mixtures containing enzyme, 124 mM HEPES buffer pH 8.0, either 5 mM Neu5Ac (cleavage) or 5 mM ManNAc and 5 mM pyruvate (condensation) at 4° C., 23° C. and 37° C. Aliquots of samples were taken out at selected intervals and the reaction stopped by adding 137 µl 2.5 mg/ml sodium periodate in 57 mM $H_2SO_4$ and further processed according to the TBA assay. The reaction was followed until there was no further change in absorbance, and hence, the reaction had reached equilibrium.

Results: Equilibrium Reaction Studies

Figure 3:
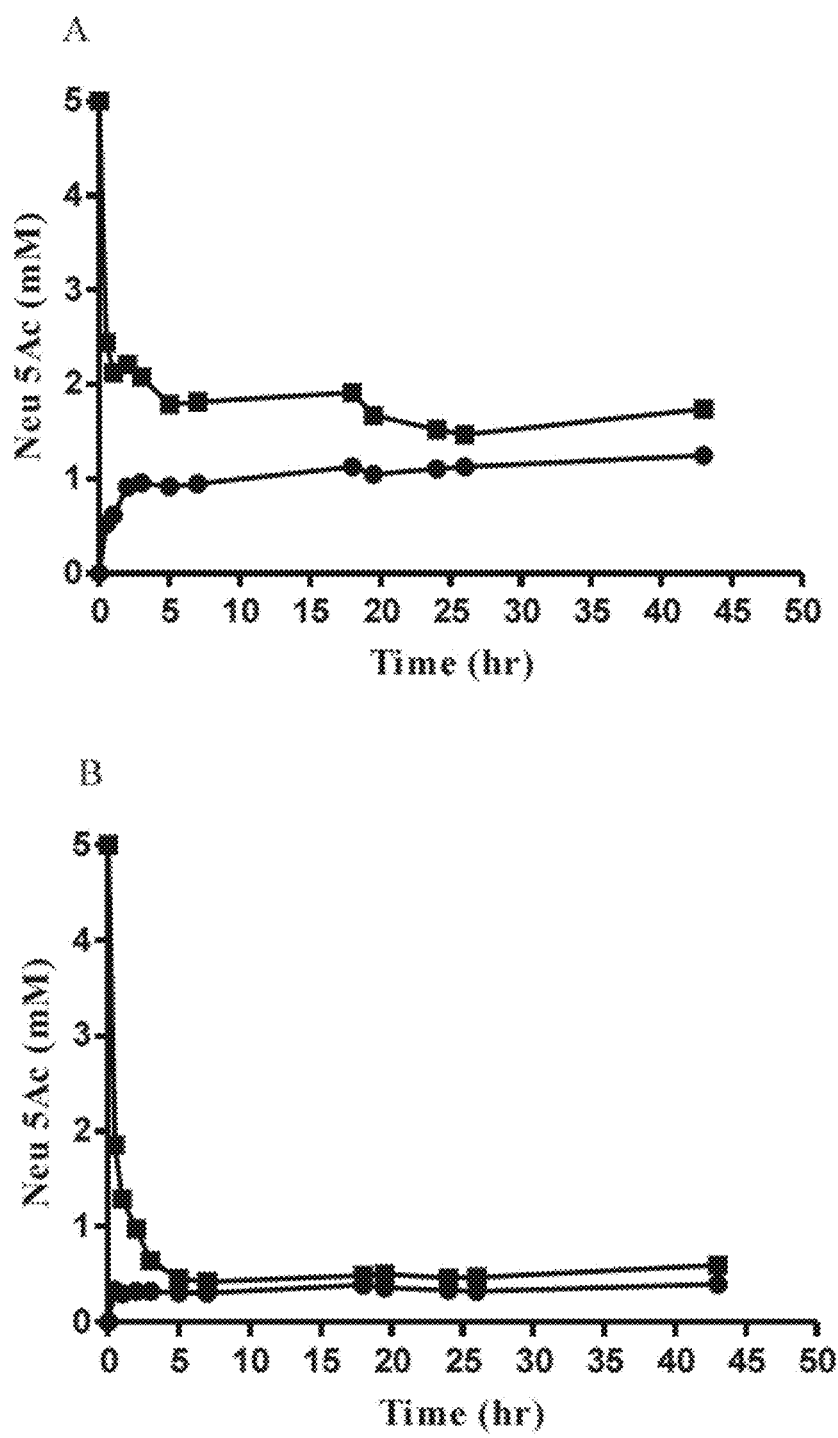
FIG. 3. Equilibrium plots of the AsNAL condensation reaction (black circles) showing amount of Neu5Ac being produced and cleavage reactions (black squares) showing amount of Neu5Ac uncleaved at different temperatures, (A) Reactions at 4° C. (B) Reactions at 23° C. (C) Reactions at 37° C.
Figure 3:
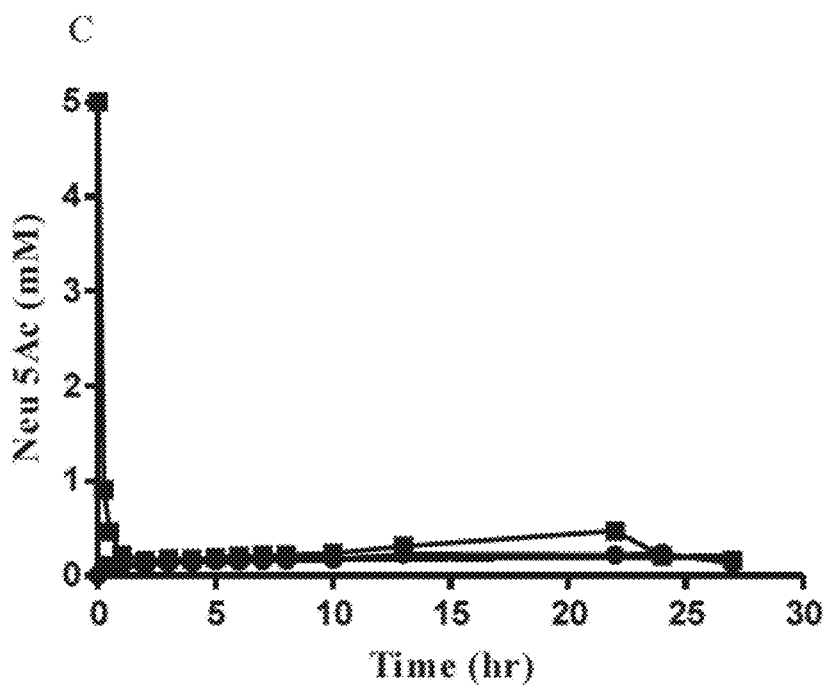

The equilibrium between reactants and products in the reactions catalyzed by AsNAL were studied at three different temperatures; 4° C., 23° C. and 37° C. (FIGS. 3A-C). The equilibrium constant for the cleavage reaction, Kc=[N-acetylmannosamine]×[pyruvate]/[N-acetylneuraminic acid], was calculated to be 0.003 at 4° C., 0.031 at 23° C. and 0.068 at 37° C. The position of the equilibrium favors the products (cleavage of Neu5Ac) (32). However at low temperature there is a substantial amount of substrate. The constant favors the formation of sialic acid by a factor of ten at 4° C. compared to room temperature, meaning that tenfold more Neu5Ac can be synthesized at lower temperatures from the same amount of substrate.

Effect of Substrate Ratio and Temperature Shift on Production Yield of Neu5Ac

The effect of substrate ratio on the conversion yield of Neu5Ac was studied by varying the pyruvate concentration while the concentration of ManNAc was kept constant. The pyruvate concentration ranged from 2.5 to 70 mM, whereas the ManNAc concentration was 5 mM, resulting in a pyruvate:ManNAc ratio ranging from 0.5 to 14. The condensation reaction mixture containing different ratios of pyruvate and ManNAc along with 124 mM HEPES buffer pH 8.0 and enzyme was incubated at room temperature for 7.5 h. The aldol condensation is an exothermic reaction, hence, lowering the temperature should increase the yield of Neu5Ac. Thus, a temperature shift experiment was carried out to see how much the Neu5Ac production could be increased by altering the equilibrium once it had been achieved. For a temperature shift experiment, the reaction mixture (enzyme, 50 mM pyruvate, 5 mM ManNAc, 124 mM HEPES buffer pH 8.0) was incubated at room temperature for 7.5 h and after reaching equilibrium it was shifted to 4° C. and incubated for 15 h. As a control, one reaction was kept at room temperature and another at 4° C. for all the time. The difference in yield between the temperature shifted and non-shifted reactions were calculated. The standard TBA assay was used to assess the activity.

Results: Effect of Substrate Ratio and Temperature Shift

Figure 4:
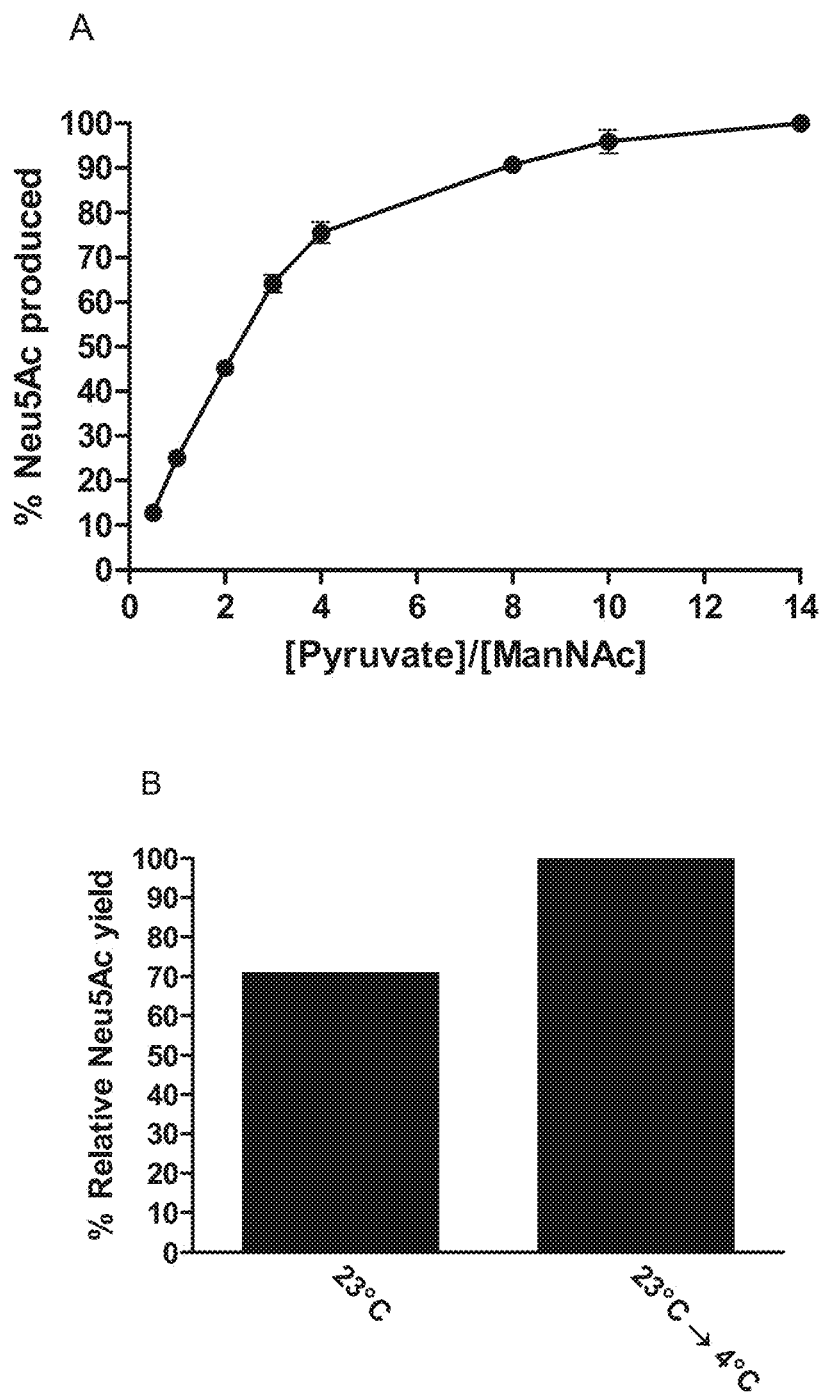
FIG. 4. Effect of [Pyruvate]:[ManNAc] ratio on the yield of N-acetylneuraminic acid (A), and the increase in N-acetylneuraminic acid production with shift in temperature from 23° C. to 4° C. (B).

A gradual increase in Neu5Ac production was observed with increasing pyruvate concentration while keeping the ManNAc concentration constant. The highest yield was observed with the ratio of 14:1 (pyruvate:ManNAc, respectively, FIG. 4A). Shifting the reaction temperature from 23° C. to 4° C., increased the yield of Neu5Ac by 30% (FIG. 4B).

Stability of AsNAL

Long term stability of AsNAL at different pH was studied by incubating the enzyme at pH values from 6.0 to 11.0 at room temperature for a month. Buffers used were Sodium phosphate (pH 6.0-7.0), HEPES (pH 7.0-8.0), Tris-HCl (pH 8.0-9.0) and glycine (pH 9.0-11.0). The enzyme activity in the condensation direction was measured using the standard reaction mixture incubated at room temperature for 1 h, with subsequent TBA assay. The stability of AsNAL at different pH was also studied using the thermofluor method described by Ericsson et al. (2006) where increased or decreased stability is related to the increase or decrease in the melting temperature of the protein. For the thermofluor assay, the protein was dialyzed overnight at 4° C. against a buffer containing 10 mM HEPES pH 7.5, 150 mM NaCl and 2 mM β-ME in Pierce Slide-A-Lyzer dialysis cassettes with a 3.5 kDa cutoff. The dialyzed protein was mixed with 2 µl of 300× Sypro® Orange protein gel stain (Sigma) and 100 mM of different buffers ranging from pH 5.0 to pH 9.0. Thermal shifts were screened for by heating in an iCycler iQ Real Time PCR Detection System (Bio-Rad Laboratories) from 1 to 80° C. in increments of 1° C./min. The buffers tested were: Sodium acetate (pH 5.0), Phosphate citrate (pH 5.0-5.5), Sodium citrate (pH 5.5), MES (pH 6.0-6.5), Na-cacodylate (pH 6.0-6.5), Sodium dipotassium phosphate (pH 6.5), BisTris (pH 7.0), HEPES (pH 7.0-8.0), Tris-HCl (pH 7.5-8.5), Imidazole (pH 7.5-8.0), Bicine (pH 8.5) and Bis-Tris propane (pH 8.5-9.0).

The melting temperature of AsNAL was studied by differential scanning calorimetry (DSC). The pure protein was dialyzed overnight at 4° C. against a buffer containing 50 mM HEPES, pH 7.5 and 500 mM NaCl in a Pierce Slide-A-Lyzer dialysis cassette (3.5 kDa cut-off). Dialyzed protein was concentrated to 1.9 mg/ml using a 10 kDa cutoff Amicon Ultra spin-column (Millipore), filtered through a 0.2 µm filter (Millipore) and degassed for 15 min. DSC experiments were carried out with a Nano-Differential Scanning Calorimeter III, (calorimetry Sciences Corporation) at a scan rate of 1° C./min in the range from 1 to 80° C. and with a constant pressure of 3 atm. The dialysis buffer was used as reference in the DSC runs. The melting temperature of the protein was calculated by subtracting the buffer-buffer baseline from the protein scan. Refolding experiments were carried out by a reverse cooling scan, allowing the unfolded protein to be kept at 4° C. overnight before a new forward scan was done. The NanoAnalyze™ software was used to calculate the melting temperature. The experimental transition curves were fitted on a two-state transition model.

Results: AsNAL Stability at Different pH Values

Figure 5:
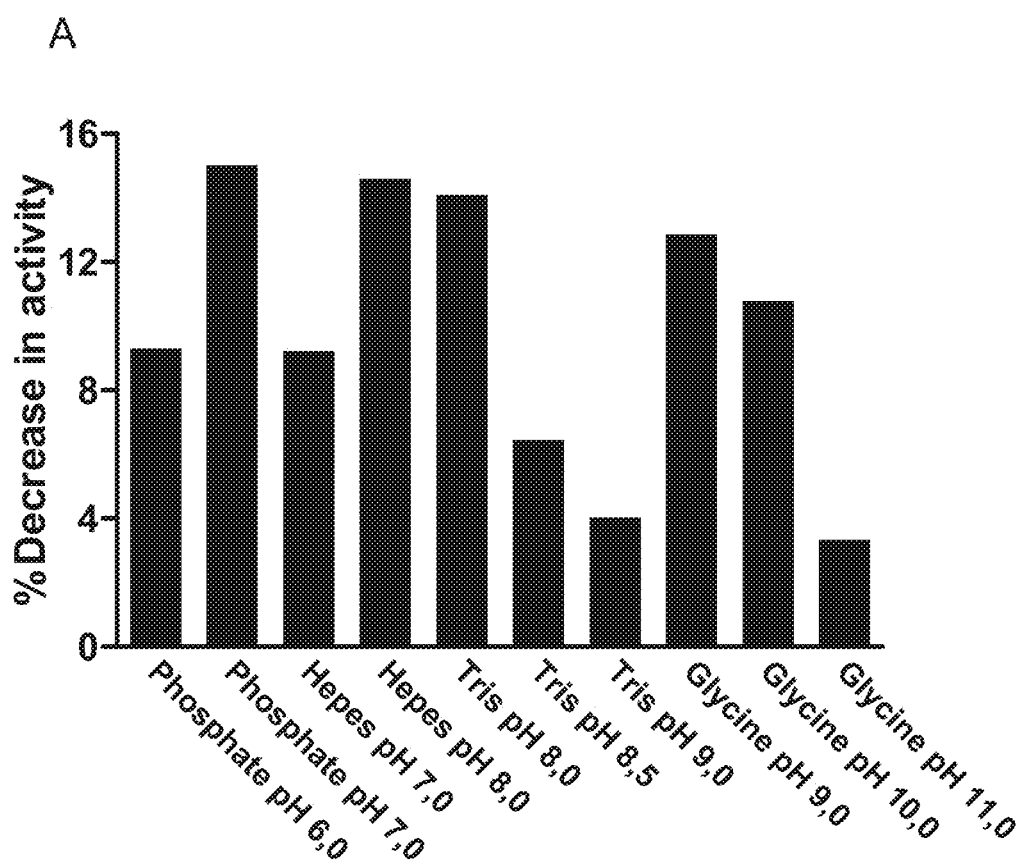
FIG. 5. Effect of pH on stability and melting temperature of AsNAL. (A) Decrease in activity of AsNAL in condensation direction incubated at different pH for one month at room temperature. Decrease in activity was calculated by subtracting the activity of 30th day from activity of 1st day. (B) Effect of pH on Tm of AsNAL. The difference in Tm was calculated by subtracting Milli-Q water Tm values.
Figure 5:
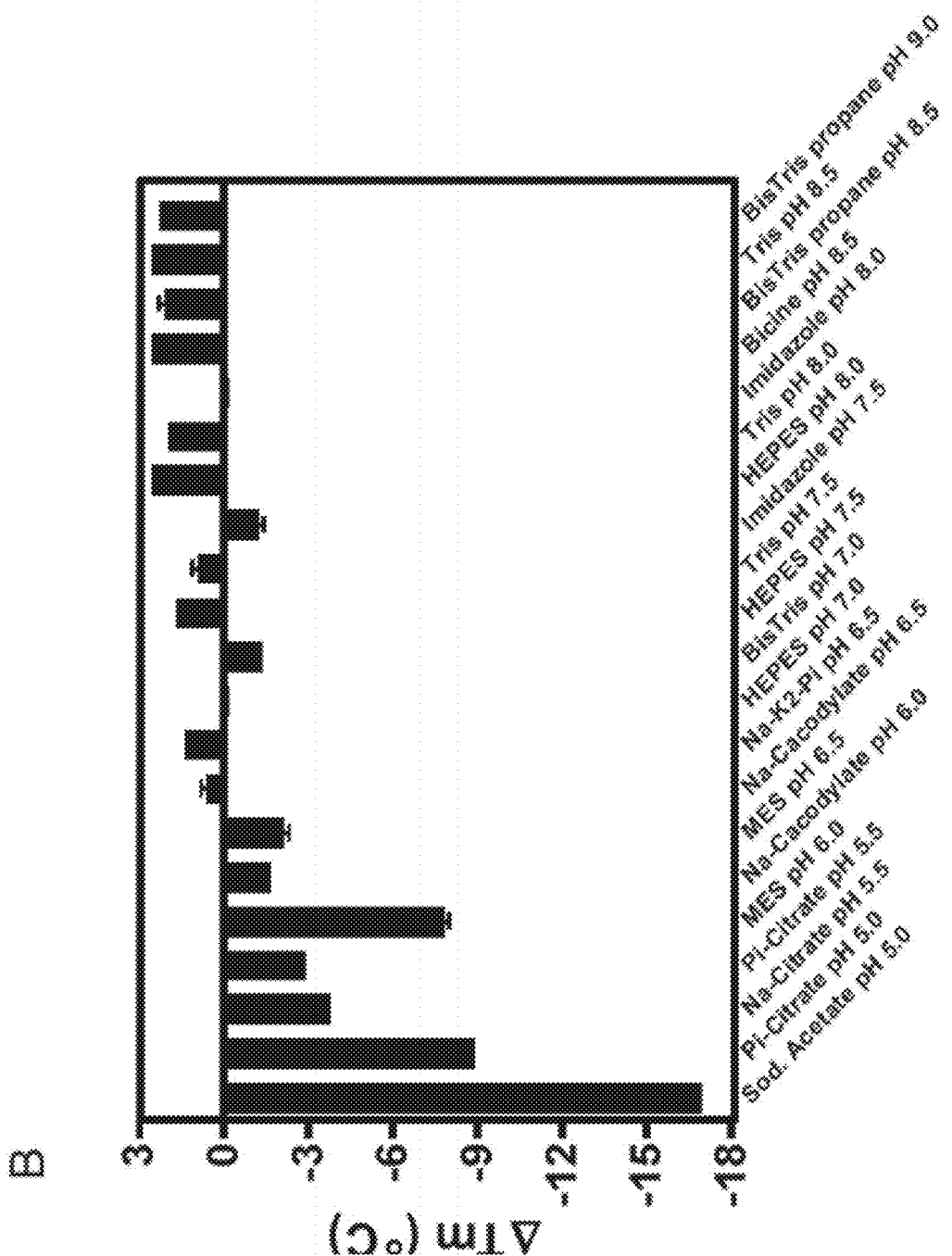

The pH-stability was investigated by incubating AsNAL in various buffers for one month (FIG. 5A). The highest decrease in activity was observed in the buffers at which the enzyme had highest activity on the first day (Phosphate pH 7.0 with 15% decrease, HEPES pH 8.0 with 14.5% decrease, Tris-HCl pH 8.0 with 14% decrease). The protein appears to be relatively stable at higher pH as interpreted from the lower decrease in activity for the condensation reaction (Tris-HCl pH 8.5, 6.4% decrease; Tris-HCl pH 9.0, 4% decrease; Glycine pH 11.0, 3.3% decrease). More than 83% of activity was retained after storage at all measured pH compared to their initial activity.

Thermal denaturation of AsNAL using the thermofluor-method was also performed to study the stability of the protein at different pH values. In milli-Q water, the melting temperature of the enzyme was 73.15±0.21° C. As a general trend, the presence of 100 mM of a low pH buffer solution decreased the melting temperature, whereas at higher pH values, the melting point was increased as shown in FIG. 5B.

Figure 6:
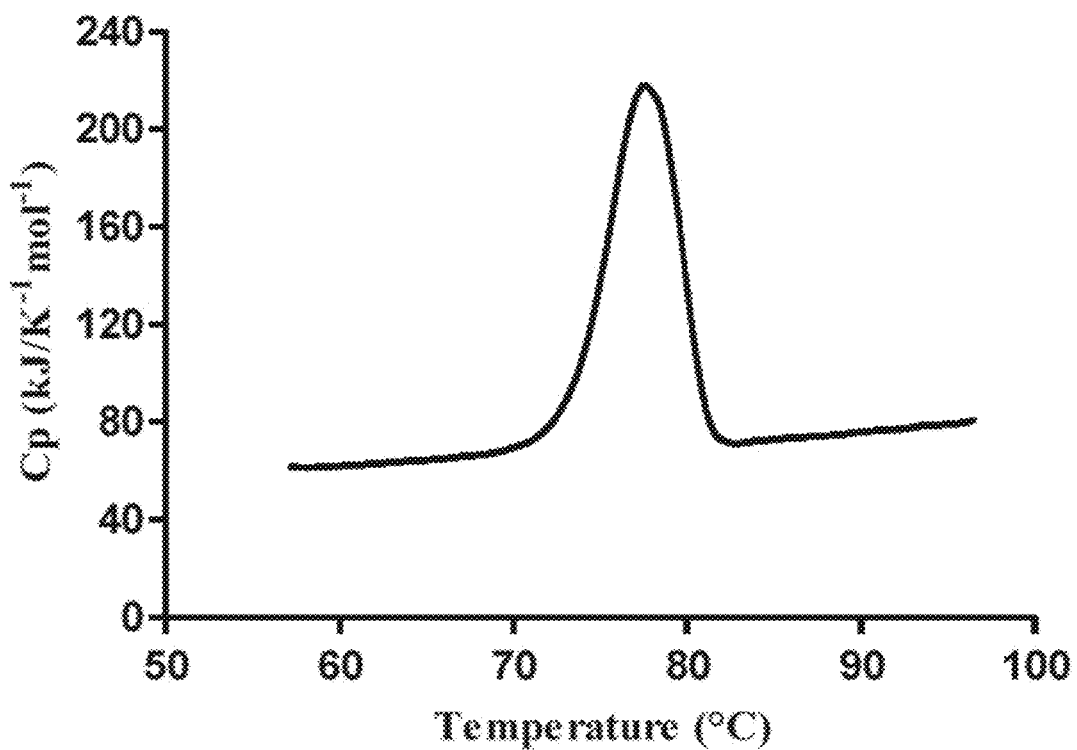
FIG. 6. Differential scanning calorimetry (DSC) profile of AsNAL showing a melting temperature of 77.5° C. at 500 mM NaCl, 50 mM HEPES pH 7.5. $\Delta H$ is 749.623 kJ/mol and $\Delta S$ is 2.137 kJ/(mol·K).

The melting temperature for AsNAL at 500 mM NaCl is 77.5° C. (FIG. 6) as determined by DSC. This is similar to that obtained from the thermofluor study (76.9° C.) at 500 mM NaCl (FIG. 5B). The protein unfolds with a single sharp peak indicating that the tetramer and each monomer unfold simultaneously.

Example 3

Comparative Studies of Specific Activity and Kinetic Constants Belonging to AsNAL and EcNAL The specific activity of AsNAL, in both directions, was compared to the specific activity of the commercially available EcNAL (Sigma) at three different temperatures: 4° C., 23° C. and 37° C.

Standard reaction mixtures were incubated at room temperature for 1 h before being subjected to the TBA assay.

Further, the enzyme kinetics for the cleavage reactions were studied using a lactate dehydrogenase (LDH)-coupled continuous assay (Comb and Roseman, 1960; Wang and Lee, 2006). The incubation mixtures contained variable amounts (1, 5, 15, 30, 45, 60, 75 and 90 mM) of Neu5Ac, 50 mM Tris-HCl, pH 8.5, 0.15 mM NADH (Sigma), 4U LDH (Sigma) and 0.315 µg of NAL in final volumes of 200 µl. Components, except the enzyme, were mixed and incubated at 37° C. for 5 min before the reactions were started by adding the specific enzyme. The measurements were done in triplicates. The decrease in absorbance at 340 nm corresponding to the oxidation of NADH by LDH in presence of released pyruvate was measured spectrophotometrically using a Spectramax M2e Microplate reader. Initial velocities were calculated using the SoftMax Pro software (Molecular Devices) and subsequently fitted to the Michaelis-Menten equation using the program GraphPad Prism 5 (GraphPad Software Inc.). The kcat values were calculated using the formula Vmax/[Enzyme]. The relationship between absorbance and substrate concentration was calculated from a standard-curve obtained by measuring the maximum absorbance from various substrate concentrations. The relationship is given by the formula: y=0.0031x+ 0.0052, where x is the pyruvate concentration. By using this formula, values of Vmax were converted from mOD/min to µM/min. Enzyme concentrations were converted from mg/ml to molar using the calculated molecular mass of 32257.9 g/mol (monomeric protein).

Results: Comparative Study

Figure 7:
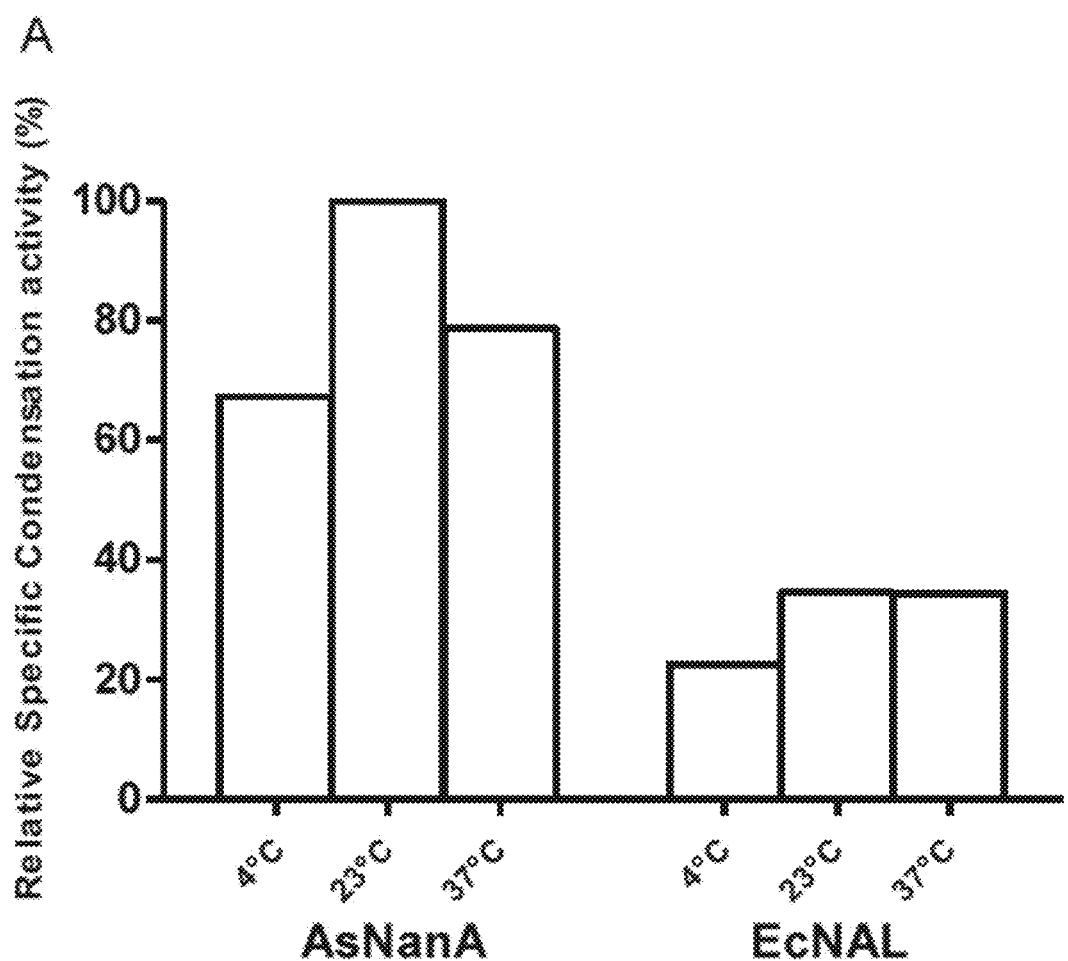
FIG. 7. Specific activity of AsNAL and EcNAL at different temperatures for the condensation reaction (A) and the cleavage reaction (B).
Figure 7:
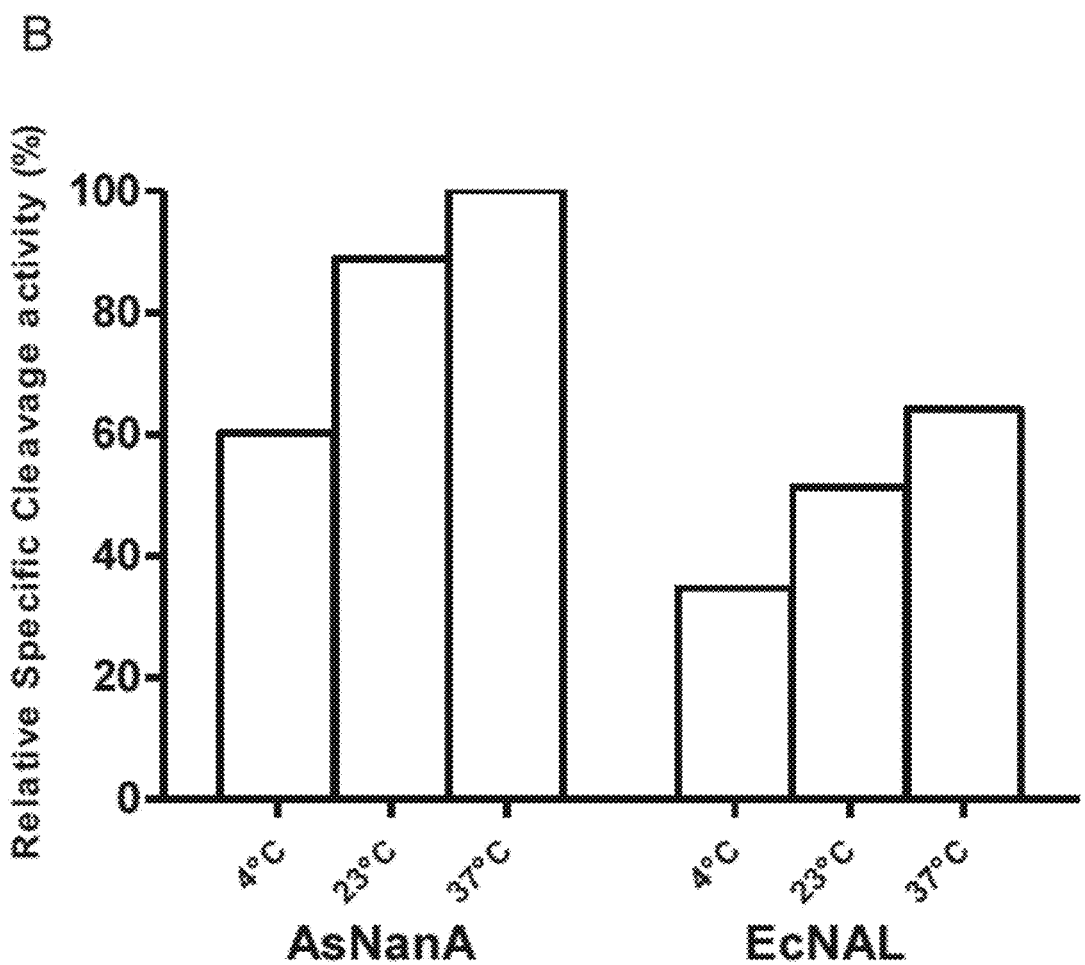

The specific activity of the condensation reaction was 40%, 60%, and 40% higher at 4° C., 23° C. and 37° C., respectively, for AsNAL than EcNAL (FIG. 7A). For AsNAL cleavage reaction it was found to be 25%, 35% and 35% higher at 4° C., 23° C. and 37° C., respectively, than for EcNAL (FIG. 7B). The presence of the His-tag in the protein did not affect the specific activity (data not shown).

Figure 8:
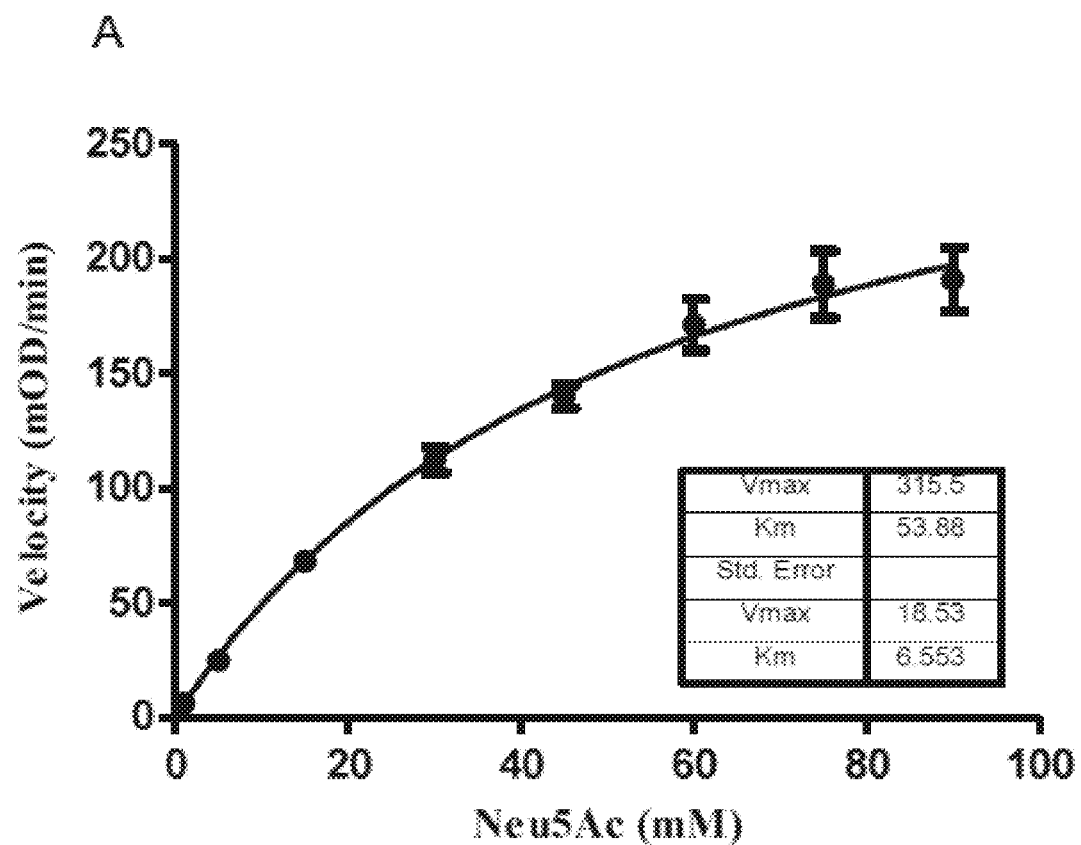
FIG. 8. Michaelis-Menten curves for AsNAL (A) and EcNAL (B) for the cleavage reaction. Initial velocities at different substrate concentrations were fitted to the Michaelis-Menten equation.
Figure 8:
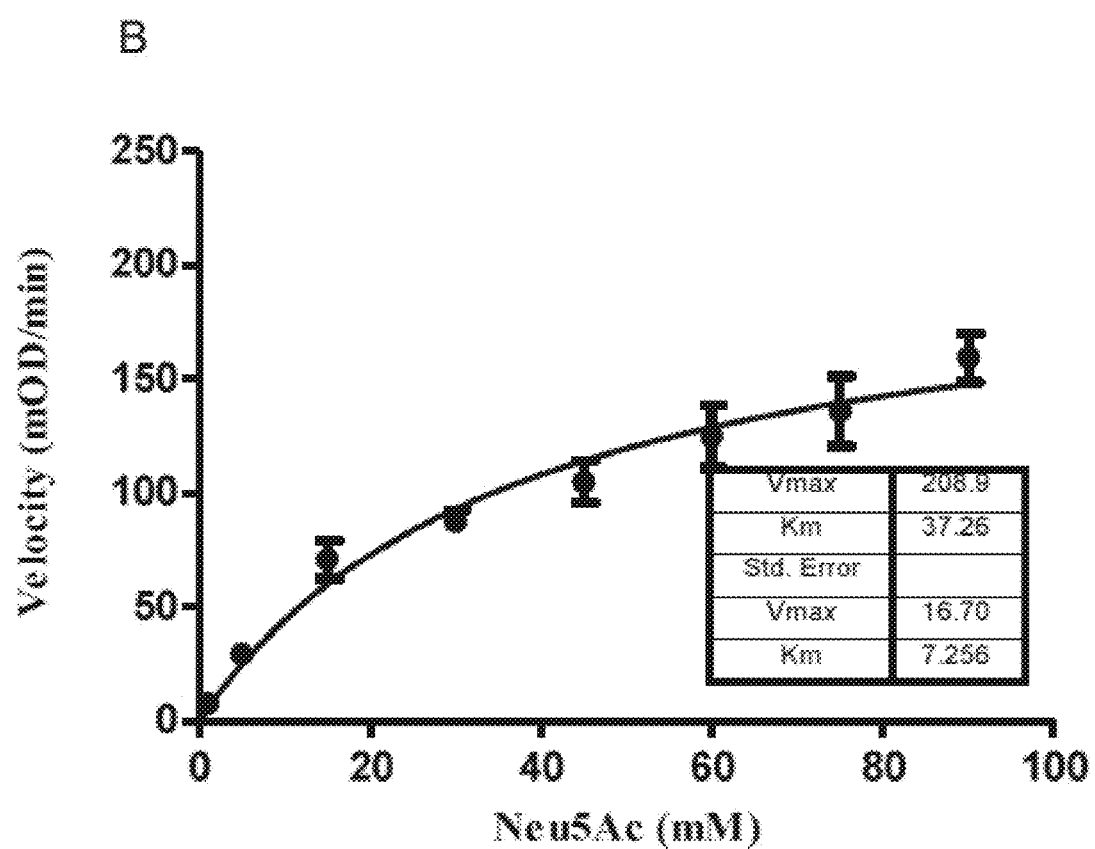

Comparison of the $K_M$, $k_{cat}$ and the catalytic efficiency of AsNAL with the values from the commercially available homologue EcNAL for the cleavage reaction are presented in Table 2 and FIG. 8. The AsNAL Michaelis constant ($K_M$) is somewhat higher than the $K_M$ obtained for EcNAL. However, the turnover number, $k_{cat}$, is strikingly higher than for EcNAL. Thus, the catalytic efficiency of AsNAL is significantly higher than EcNAL.

TABLE 2

Kinetic data for AsNAL and EcNAL

| Source | Substrate | $V_{max}$ | $K_M$ (mM) | $k_{cat}$ (min$^{-1}$) | $k_{cat}/K_M$ (mM$^{-1}$ min$^{-1}$) |
|---|---|---|---|---|---|
| AsNAL | Neu5Ac | 315.5 ± 18.5 | 53.88 ± 6.55 | 1146.26 | 21.27 |
| EcNAL | Neu5Ac | 208.9 ± 16.7 | 37.26 ± 7.25 | 192.22 | 5.15 |

Example 4

Integrated Reaction 20 mM of N-acetylglucosamine (GlcNAc) or N-acetylmannosamine (ManNAc), 80 mM of pyruvate, 7 µg of enzyme (AsNAL or EcNAL), 124 mM buffer and dH$_2$O were mixed in a tube to a total volume of 250 µl. For ManNAc reactions, the buffer used was HEPES, pH 8.0. For GlcNAc reactions, the buffer used was CAPS pH 11.0. Experiments were performed in triplicate. For ManNAc experiments, aliquots were sampled after 0.5, 1.0, 1.5, 2.5 and 4.0 h. For GlcNAc experiments, aliquots were sampled after 12, 24, 36, 48 and 72 h. Reactions were terminated by addition of 2 µl concentrated H$_2$SO$_4$. The time needed for N-acetylneuraminic acid (Neu5Ac) production to get started under these conditions was known to take longer time based on initial test experiments. The thiobarbituric acid (TBA) assay procedure was followed to determine the amount of Neu5Ac produced. The activity was corrected for a blank value. The blank contained all the reaction components except for enzyme.

Initially, also glycine buffer was tested at pH 10.5 and pH 11.0 for the reactions with GlcNAc. GlcNAc will chemically epimerize to ManNAc at pH values above 9.0, which the enzyme will use as substrate for the production of Neu5Ac. The epimerization is pH dependent and will increase with increasing pH. Production of Neu5Ac was higher in CAPS buffer compared to glycine buffer, so this was chosen for further experiments. Production of Neu5Ac was higher at pH 11.0 compared to pH 10.5 for both ecNAL and asNAL, further experiments were therefore performed at pH 11.0, and also tested at pH 11.5 in one parallel.

Figure 9:
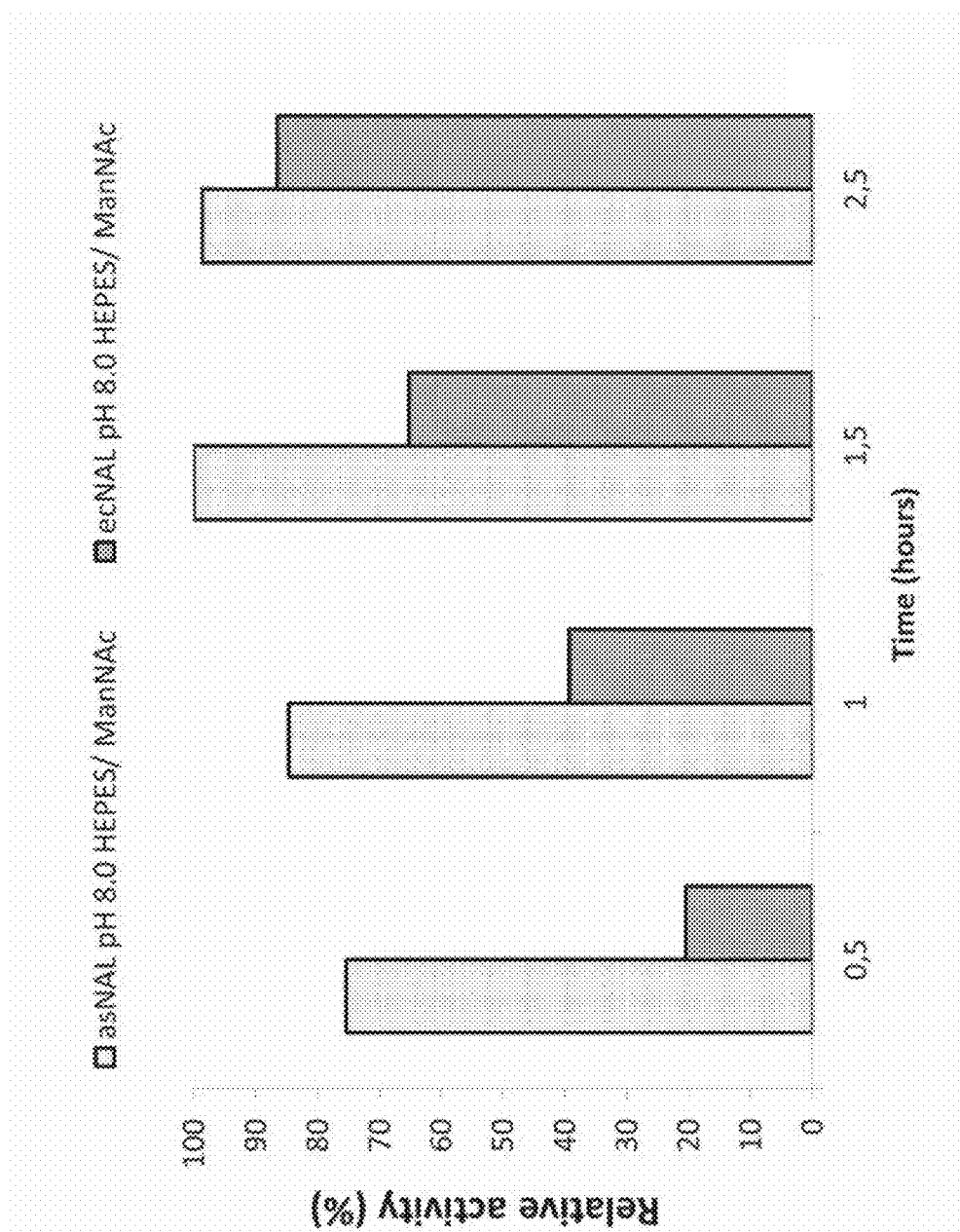
FIG. 9. Production of N-acetylneuraminic acid by asNAL and EcNAL by incubation of 7 μg of the enzymes with 80 mM pyruvate and 20 mM ManNAc in 124 mM of HEPES buffer, pH 8.0.

The experiments with ManNAc and the optimal buffer from the pH activity experiments (HEPES, pH 8.0) were performed for comparison of amount of Neu5Ac produced. Results: The production of Neu5Ac when using pyruvate and ManNAc in a 4:1 ratio at pH 8.0 was highest after 1.5 h of incubation for asNAL. This value was set to 100%. From FIG. 9, it is seen that asNAL is a more efficient enzyme compared to ecNAL where the production of Neu5Ac starts off earlier in time. The difference between the two enzymes is highest at the earliest time points, the production of Neu5Ac by ecNAL increases gradually over time, but never reaches the same level as for asNAL. After 4 h of incubation the production levels off for both enzymes (not shown). This might be due to completed reactions.

Figure 10:
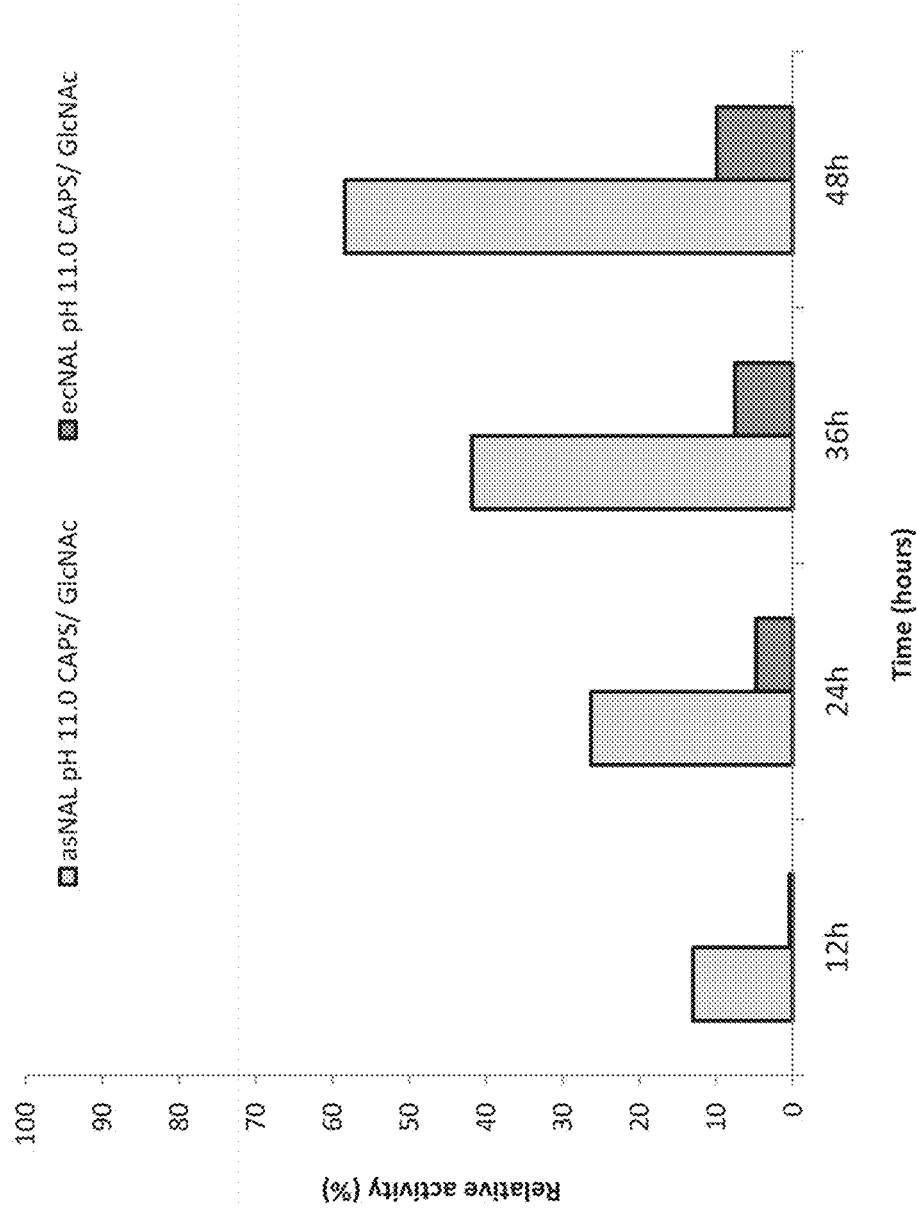
FIG. 10. Integrated reaction: Production of N-acetylneuraminic acid by asNAL and EcNAL by incubation of 7 μg of the enzymes with 80 mM pyruvate and 20 mM GlcNAc in 124 mM of CAPS buffer, pH 11.0.

The production of Neu5Ac when using pyruvate and GlcNAc in a 4:1 ratio at pH 11.0 was compared to the previous experiment, and is shown in FIG. 10. The production is low for ecNAL at this pH value. For asNAL, the production increases after 12 h and thereafter increases gradually up to 48 h. After 72 h of incubation the production levels off also for asNAL (not shown). This might be due to a completed reaction and degradation of product may have started. The production is highest after 48 h of incubation for asNAL and corresponds to around 60% of the highest amount obtained when using pyruvate and ManNAc in a 4:1 ratio at pH 8.0.

Figure 11:
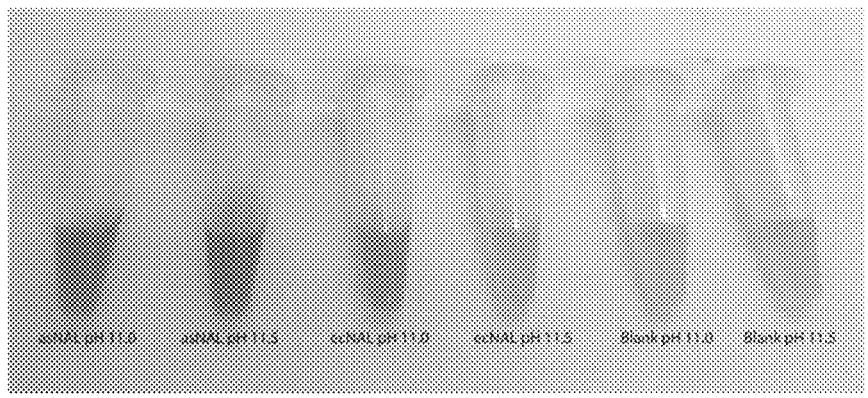
FIG. 11. Production of N-acetylneuraminic acid by asNAL and EcNAL by incubation of 7 μg of the enzymes with 80 mM pyruvate and 20 mM GlcNAc in 124 mM of CAPS buffer at pH 11.0 and 11.5. In the TBA assay, production of a red chromophore giving absorbance at 549 nm is due to the presence of Neu5Ac.

We also tested production of Neu5Ac at pH 11.5 for the two enzymes. At this pH, no production was observed for ecNAL, whereas asNAL still was able to produce Neu5Ac in the same range as at pH 11.0 (FIG. 11).

Example 5

Production of Neu5,7Ac2/Neu5,8Ac2/Neu5,9Ac2 and Legionaminic Acid 15 mM of 4-O-acetyl-2-N-acetylmannosamine (4-OAc-ManNAc) or 2,4-diacetamino-2,4,6-trideoxymannose, 15 mM of pyruvate, 28 µg of enzyme (AsNAL), 124 mM HEPES buffer, pH 8.0 and dH2O were mixed in a tube to a total volume of 200 µl. Aliquots were sampled after 1.0, 1.5 and 4.0 h for production of di-acetylated Neus. For production of Legionaminic acid aliquots were sampled after 1.0 and 3.0 h. Reactions were terminated by addition of 2 µl concentrated H2SO4. Samples were passed over Amicon Ultra spin-columns with a 10000 molecular weight cut-off (Millipore) to remove high molecular weight compounds. The low molecular weight fractions were then used in DMB-HPLC coupled to mass spectrometric analyses. Derivatization of samples with DMB were performed according to protocol given by the supplier (Sialic Acid Fluorescence Labeling Kit, Takara Inc.). Reactions were carried out for 2.5 hours at 50° C. in the dark. A reference panel with a mixture of the Sias; Neu5Gc, Neu5Ac, Neu5, 7Ac2, Neu5Gc9Ac, Neu5,9Ac2 and Neu5, (7/8)9Ac3 (ProZyme Inc.) were also subjected to derivatization with DMB. DMB-labeled sialic acids were separated by HPLC using Accela HPLC (Thermo Scientific) on a LTQ Orbitrap XL Fourier Transform Mass Spectrometer (FTMS) with an Electrospray ion source (Thermo Scientific) using a positive ion profile mode fullscan (+pESI). The column used was a Hypersil Gold 50×2.1 mm, 1.9 μm reversed-phase C18 column (Thermo scientific).). Elution was achieved using water with 0.1% formic acid (A) and acetonitrile with 0.1% formic acid (B) at a flow rate of 400 μl/min.

The gradient table used is presented in Table 3.

TABLE 3

Analysis LC-MS, gradient table
Gradient: A: H20 w. 0.1% formic acid
B: Acetonitrile w. 0.1% formic acid
Flow: 400 ul/min

| Time | % A | % B |
|---|---|---|
| 0.00 | 95 | 5 |
| 1.00 | 95 | 5 |
| 8.00 | 75 | 25 |
| 8.01 | 10 | 90 |
| 9.00 | 10 | 90 |

TABLE 3-continued

Analysis LC-MS, gradient table
Gradient: A: H20 w. 0.1% formic acid
B: Acetonitrile w. 0.1% formic acid
Flow: 400 ul/min

| Time | % A | % B |
|---|---|---|
| 9.01 | 95 | 5 |
| 10.00 | 95 | 5 |

The analytical conditions were set to 300° C. for capillary temperature, 4.5 kV spray voltage, m/z 350-550 scan range and 35% collision energy. The MS/MS was targeted on the masses m/z 426.15, m/z 468.16 and m/z 451.18 using Ion trap MS (ITMS)+cESI with full MS2 in scan range m/z 125-480, corresponding to the DMB derivates DMB-Neu5Ac, DMB-di-acetylated Neu and DMB-Leg.

Results Using 4-O-acetyl-2-N-acetylmannosamine as a Substrate:

The substrate 4-OAc-ManNAc is fairly stable in dry conditions and is dissolved in dH20 immediately before use. Acetyl migration from the 4 to the 6 position is a side reaction that could occur in basic and in acidic conditions, while in neutral aqueous solution it should be stable. Additionally, the acetyl group in the 7th position of Neu5,7Ac2 may undergo migration to the more stable 9th position. Without being bound by theory, this migration of the acetyl group is likely to occur via the $8^{th}$ position which may explain the presence of Neu5,8Ac2 after the reaction is complete. While Neu5,7Ac2 will be formed if 4-OAc-ManNAc is the substrate, Neu5,9Ac2 will be formed if 6-OAc-ManNAc is the substrate.

Figure 12A:
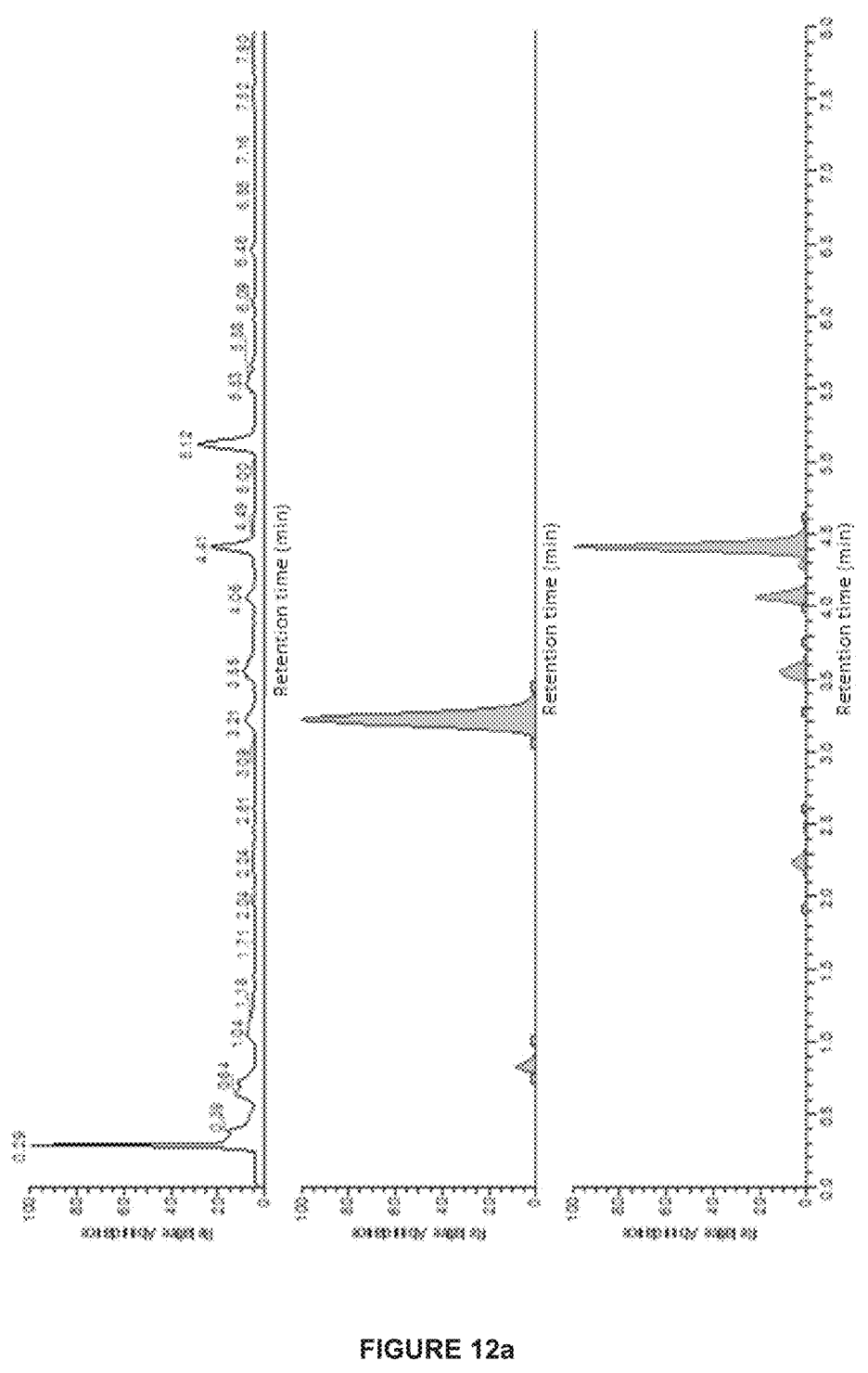
Figure 12B:
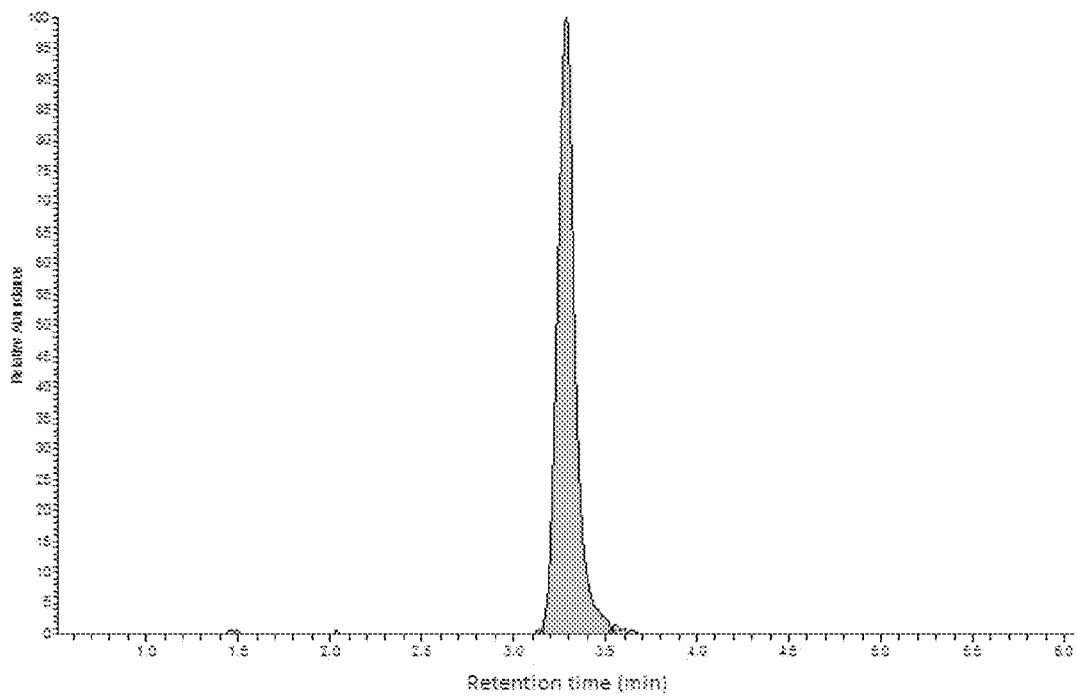
FIG. 12b. Production of legionaminic acid by asNAL by incubation of 28 μg of the enzyme with 15 mM of pyruvate and 15 mM of 2,4-diacetamino-2,4,6-trideoxymannose in 124 mM HEPES buffer at pH 8.0. Aliquots were sampled after 1 h. Reactions were terminated by addition of 2 μl concentrated H2SO4. The low molecular weight fractions were then derivatizated with DMB according to protocol given by the supplier. DMB-labeled sialic acids were separated by HPLC. The peak at RT 3.29 corresponds to legionaminic acid.

Even though the enzymatic reaction is performed at pH 8, formation of both Neu5,9Ac2 (RT 4.4 in FIG. 12*a*), Neu5,7Ac2 (RT 3.56 in FIG. 12*a*) and Neu5,8Ac2 (RT 4.05 in FIG. 12*a*) were observed. The reaction also produced some Neu5Ac, which probably is caused by loss of acetyl group from some of the substrate.

The production of Neu5,9Ac2, Neu5,7Ac2 and Neu5,8Ac2 when using pyruvate and 4-O-acetyl-2-N-acetylmannosamine at pH 8.0 was highest after 4 h of incubation with asNAL, see table 4. Production of Neu5,9Ac2, Neu5,7Ac2 and Neu5,8Ac2 is around 30-40% of what is observed using ManNAc as a substrate under same conditions.

TABLE 4

Results of the enzymatic reaction

| Sample Name | Descr. | 468.1613@3.56 | | 468.1613@4.05 | | 468.1613@4.4 | |
|---|---|---|---|---|---|---|---|
| | | Area | RT | Area | RT | Area | RT |
| Blank H20 | | NF | NF | NF | NF | NF | NF |
| 1: Neg control | 4OAc-ManNAc rxn without aldolase | NF | NF | NF | NF | NF | NF |
| 2A | 4OAc-ManNAc rxn-1 hour | 3258981 | 3.52 | 4611697 | 4.05 | 20834893 | 4.39 |
| 3A | 4OAc-ManNAc rxn-1.5 hours | 4048804 | 3.54 | 5467510 | 4.06 | 23706892 | 4.40 |
| 4A | 4OAc-ManNAc rxn-4 hours | 4484920 | 3.54 | 6019425 | 4.07 | 26500427 | 4.41 |
| Standardpanel 0.500 nmol | | 387962 | 3.55 | 279532 | 4.07 | 2627574 | 4.41 |

Area: Relative amounts presented as the area under the curve defined by the given RT value, see FIG. 12a.
RT: Retention time (DMB-labeled sialic acids separated by HPLC), see FIG. 12a.
168.1613@3.56: Neu5,7Ac2
168.1613@4.05: Neu5,8Ac2
168.1613@4.4: Neu5,9Ac2
NF Not found Results Using 2,4-diacetamino-2,4,6-trideoxymannose as a Substrate:

The results shown in table 5 demonstrates that AsNAL is able to produce legionaminic acid using 2,4-diacetamino-2,4,6-trideoxymannose as a substrate. The production of legionaminic acid was highest after 3 h of incubation with asNAL, see table 5.

TABLE 5

Results of the enzymatic reaction

| Sample | RT 3.29 (Area) |
|---|---|
| 2,4-diacetamino-2,4,6-trideoxymannose 1 h | 902252 |
| 2,4-diacetamino-2,4,6-trideoxymannose 3 h | 1663378 |

Area: Relative amounts presented as the area under the curve defined by the given RT value, see figure 12b.
RT: Retention time (DMB-labeled sialic acids separated by HPLC), see figure 12b.

Example 6

Cleavage of N-glycolylneuraminic Acid (Neu5Gc) and 2-keto-3-deoxy-D-glycero-D-galacto-nononic Acid (KDN)

The cleavage reaction of AsNAL contained 6.6 µg of AsNAL, 5 mM Neu5Gc or KDN and 124 mM HEPES buffer pH 8.0. For blank ($H_2O$) and positive control the same components of the reactions were used, but the amount of enzyme was replaced by assay buffer. All reactions were filled up to a total volume of 50 µL with dH2O. The assay was performed in triplicate. After 1 h incubation at room temperature, the enzyme reaction was stopped by adding 2 µL concentrated H2SO4. The thiobarbituric acid (TBA) assay procedure was followed to determine the amount cleaved.

Results:

The results shown in table 6 demonstrates that AsNAL is able to cleave both Neu5Ac, Neu5Gc and KDN (2-keto-3-deoxy-D-glycero-D-galacto-nononic acid).

TABLE 6

Results of the enzymatic reaction

| Substrate | OD sample-blank (measures uncleaved substrate) | OD Positive control (minus enzyme) | Cleaved | % cleaved |
| --- | --- | --- | --- | --- |
| Neu5Ac | 1.048 ± 0.016 | 6.032 | 4.984 ± 0.016 | 82.6 |
| Neu5Gc | 1.422 ± 0.076 | 5.440 | 4.018 ± 0.076 | 73.9 |
| KDN | 2.662 ± 0.130 | 5.320 | 2.658 ± 0.130 | 50.0 |

LIST OF REFERENCES CITED IN THE DESCRIPTION

Auge C. et al. (1984). "Synthesis with immobilized enzyme of the most important sialic acid." *Tetrahedron Letters* 25: 4663-4664.

Aminoff D. (1961). "Methods for the quantitative estimation of N-acetylneuraminic acid and their application to hydrolysates of sialomucoids." *Biochem J.* 81: 384-92.

Blayer S. et al. (1999). "Alkaline biocatalysis for the direct synthesis of N-acetyl-D-neuraminic acid (Neu5Ac) from N-acetyl-D-glycosamine (GlcNAc)." *Biotechnol Bioeng* 66(2): 131-136.

Brug J. and Paerels G. B. (1958). "Configuration of N-acetylneuraminic acid." *Nature* 182(4643): 1159-60.

Comb D. G. and Roseman S. (1958). "Composition and enzymatic synthesis of N-acetylneuraminic acid (sialic acid)." *Journal of the American Chemical Society* 80: 497-499.

Comb D. G. and Roseman S. (1960). "The sialic acids. I. The structure and enzymatic synthesis of N-acetylneuraminic acid." *J Biol Chem* 235: 2529-37

Ericsson U. B. et al. (2006). "Thermofluor-based high-throughput stability optimization of proteins for structural studies." *Anal Biochem* 357(2): 289-298.

Gurung M. K. (2013). "Characterization of the sialic acid synthase from *Aliivibrio salmonicida* suggests a novel pathway for bacterial synthesis of 7-O-acetylated sialic acids." *Glycobiology* 23(7): 806-19.

Koeller K. M. and Wong C. H. (2001). "Enzymes for chemical synthesis." *Nature* 409(6817): 232-40.

Machajewski T. D. and Wong C. H. (2000). "The Catalytic Asymmetric Aldol Reaction." *Angew Chem Int Ed Engl.* 39(8): 1352-1375.

Wang T.-H. and Lee W.-C. (2006). "Production of 2-keto-3-deoxy-d-glycero-d-galacto-nonopyranulosonic acid (KDN) using fusion protein of N-acetyl-d-neuraminic acid aldolase." *Biochemical Engineering Journal* 29: 75-80

Warren L. (1959). "The thiobarbituric acid assay of sialic acids." *J Biol Chem* 234(8): 1971-5.

Warren L. and Felsenfeld H. (1962). "The biosynthesis of sialic acids." *J Biol Chem.* 237: 1421-31.

---

The invention claimed is:

1. A method for the production of neuraminic acid or a derivative thereof comprising:
   a) transforming glucosamine or a derivative thereof into mannosamine or a derivative thereof by epimerization at an alkaline pH above 9; and
   b) reacting mannosamine or the derivative thereof with pyruvate at an alkaline pH of at least 9.5 in the presence of a polypeptide comprising the amino acid sequence as set forth in SEQ ID NO: 1 or a functional variant thereof; wherein the functional variant is a polypeptide comprising an amino acid sequence having at least 90% sequence identity to the amino acid sequence set forth in SEQ ID NO: 1.

2. A method for the production of neuraminic acid or a derivative thereof comprising:
   reacting mannosamine or a derivative thereof with pyruvate at an alkaline pH of at least 9.5 in the presence of a polypeptide comprising the amino acid sequence as set forth in SEQ ID NO: 1 or a functional variant thereof; wherein the functional variant is a polypeptide comprising an amino acid sequence having at least 90% sequence identity to the amino acid sequence set forth in SEQ ID NO: 1.

3. The method according to claim 2, wherein the functional variant is a polypeptide comprising an amino acid sequence having at least 95% sequence identity to the amino acid sequence set forth in SEQ ID NO: 1.

4. The method according to claim 2, wherein the alkaline pH in the reacting step is in the range from 9.5 to 12.

5. The method according to claim 1, wherein the alkaline pH in the transforming step is in the range from 9.5 to 12.

6. The method according to claim 1, wherein the transforming step is performed at the same pH or within the same pH range as in the reacting step.

7. The method according to claim 1, wherein the transforming step is carried out at a temperature ranging from 45 to 70° C.

8. The method according to claim 1, wherein the transforming step is carried out at the same temperature or within the same temperature range as in the reacting step.

9. The method according to claim 8, wherein the reacting step and the transforming step are carried out at a temperature ranging from 15 to 25° C.

10. The method according to claim 2, wherein in the reacting step the ratio of pyruvate to mannosamine or a derivative thereof is in the range from 1:1 to 14:1.

11. The method according to claim 2, wherein the derivative of neuraminic acid is an N-substituted neuraminic acid.

12. The method according to claim 1, wherein the derivative of glucosamine is GlcNAc, and wherein the derivative of neuraminic acid and the derivative of mannosamine are selected from the group consisting of:
- the derivative of neuraminic acid is Neu5Ac and the derivative of mannosamine is ManNAc;
- the derivative of neuraminic acid is legionaminic acid and the derivative of mannosamine is 2,4-diacetamino-2,4,6-trideoxymannose;
- the derivative of neuraminic acid is Neu5,7Ac2, Neu5,8Ac2, Neu5,9Ac2 or any mixture thereof and the derivative of mannosamine is 4-0-acetyl-2-N-acetylmannosamine, 6-0-acetyl-2-N-acetylmannosamine or any mixture thereof;
- the derivative of neuraminic acid is Neu5Gc and the derivative of mannosamine is N-glycolylmannosamine; and
- the derivative of neuraminic acid is 2-keto-3-deoxy-D-glycero-D-galacto-nononic acid and the derivative of mannosamine is D-mannose.

* * * * *